(12) United States Patent
Eberlein et al.

(10) Patent No.: US 7,407,963 B2
(45) Date of Patent: Aug. 5, 2008

(54) CYCLOPROPANE CGRP ANTAGONISTS, MEDICAMENTS CONTAINING THESE COMPOUNDS, AND METHOD FOR THE PRODUCTION THEREOF

(75) Inventors: Wolfgang Eberlein, Biberach (DE); Wolfhard Engel, Biberach (DE); Klaus Rudolf, Warthausen (DE); Henri Doods, Warthausen (DE); Gerhard Hallermayer, Maselheim-Sulmingen (DE); Eckhart Bauer, Biberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 11/169,078

(22) Filed: Jun. 27, 2005

(65) Prior Publication Data

US 2005/0267137 A1 Dec. 1, 2005

Related U.S. Application Data

(63) Continuation of application No. 10/121,872, filed on Apr. 12, 2002, now abandoned, which is a continuation of application No. PCT/EP00/10391, filed on Oct. 29, 1999.

(30) Foreign Application Priority Data

Oct. 29, 1999 (DE) ................................ 199 52 147

(51) Int. Cl.
| A61K 31/517 | (2006.01) |
| A61K 31/454 | (2006.01) |
| C07D 403/02 | (2006.01) |
| C07D 239/72 | (2006.01) |

(52) U.S. Cl. ............................. 514/266.22; 514/266.3; 514/264.1; 514/293; 514/322; 514/384; 514/386; 544/279; 544/285; 546/82; 546/84; 546/199

(58) Field of Classification Search ............ 514/252.03, 514/255.05, 256, 314, 318, 326, 266.22, 514/266.3, 264.1, 293, 322, 384, 386; 544/238, 544/333, 405, 279, 285; 546/176, 194, 209, 546/210, 211, 213, 214, 82, 84, 199
See application file for complete search history.

(56) References Cited

U.S. PATENT DOCUMENTS

| 3,655,667 | A | * | 4/1972 | Kniser et al. ................ 544/392 |
| 3,873,707 | A | * | 3/1975 | Welstead, Jr. ............... 514/327 |
| 5,741,791 | A | | 4/1998 | Olsen |
| 6,019,967 | A | | 2/2000 | Breton et al. |
| 6,344,449 | B1 | | 2/2002 | Rudolf et al. |
| 2002/0128206 | A1 | * | 9/2002 | Hay et al. ..................... 514/19 |
| 2003/0018021 | A1 | * | 1/2003 | Kornberg et al. ........ 514/210.02 |
| 2003/0134840 | A1 | * | 7/2003 | Baxter et al. ............. 514/210.2 |
| 2003/0176460 | A1 | * | 9/2003 | Howe et al. ................. 514/316 |
| 2003/0191110 | A1 | * | 10/2003 | Botfield et al. ......... 514/211.15 |
| 2003/0229121 | A1 | * | 12/2003 | Du Bois et al. ............. 514/317 |
| 2003/0236282 | A1 | * | 12/2003 | Hurnaus et al. ............. 514/314 |

FOREIGN PATENT DOCUMENTS

| CA | 2361939 A1 | 9/2000 |
| CA | 2378428 A1 | 2/2001 |
| EP | 0723774 A1 | 7/1996 |
| WO | 9722338 A1 | 6/1997 |
| WO | 9811128 A1 | 3/1998 |
| WO | WO 98/09630 | 3/1998 |
| WO | 9852940 A1 | 11/1998 |
| WO | WO 99/47517 | 9/1999 |
| WO | 0055154 A1 | 9/2000 |
| WO | 0110425 A2 | 2/2001 |

* cited by examiner

Primary Examiner—James O. Wilson
Assistant Examiner—Tamthom N Truong
(74) Attorney, Agent, or Firm—Michael P. Morris; Mary-Ellen M. Devlin; Alan R. Stempel

(57) ABSTRACT

A compound of general formula (I)

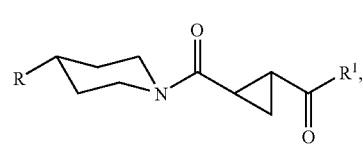

(I)

wherein R and $R^1$ are as defined herein, or a tautomer, diastereomer, enantiomer, or salt thereof, particularly the physiologically acceptable salts thereof, which have valuable pharmacological properties, particularly CGRP-antagonistic properties, pharmaceutical compositions containing the compound, their use, and processes for preparing them.

28 Claims, No Drawings

CYCLOPROPANE CGRP ANTAGONISTS, MEDICAMENTS CONTAINING THESE COMPOUNDS, AND METHOD FOR THE PRODUCTION THEREOF

RELATED APPLICATIONS

This application is a continuation of application 10/121,872 filed on Apr. 12, 2002, now abandoned which is a continuation of International Application No. PCT/EP00/10391, filed on 21 Oct. 2000, benefit of which is hereby claimed, pursuant to 35 U.S.C. § 365(c) and § 120.

BACKGROUND OF THE INVENTION

The present invention relates to new cyclopropanes of general formula

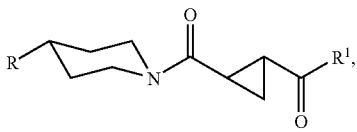

the tautomers, the diastereomers, the enantiomers, the mixtures thereof and the salts thereof, particularly the physiologically acceptable salts thereof with inorganic or organic acids or bases, pharmaceutical compositions containing these compounds, their use and processes for preparing them.

In the above general formula (I)

R denotes a saturated or mono- or diunsaturated 5- to 7-membered aza, diaza, triaza, oxaza, thiaza, thiadiaza, or S,S-dioxido-thiadiaza heterocyclic group, whilst the abovementioned heterocyclic groups are linked via a carbon or nitrogen atom, and may contain one or two carbonyl groups adjacent to a nitrogen atom, may be substituted by an alkyl group at one of the nitrogen atoms, may be substituted at one or two carbon atoms by a straight-chain or branched alkyl group, by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl, or 1-methylimidazolyl group, whilst the substituents may be identical or different, and wherein an olefinic double bond of one of the abovementioned unsaturated heterocyclic groups may be fused with a benzene, pyridine, diazine, 1,3-oxazole, thiophene, furan, thiazole, pyrrole, N-methylpyrrole, quinoline, imidazole, or N-methylimidazole ring, while the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl, or 1-methylimidazolyl groups contained in R and the benzo-, thieno-, pyrido-, and diazino-fused heterocyclic groups in the carbon skeleton may additionally be mono-, di-, or trisubstituted by fluorine, chlorine, or bromine atoms, by alkyl, dialkylaminoalkoxy, nitro, alkylthio, alkylsulfinyl, alkylsulfonyl, alkylsulfonylamino, phenyl, trifluoromethyl, alkoxycarbonyl, alkoxycarbonylalkyl, alkoxycarbonylalkoxy, hydroxycarbonylalkoxy, carboxy, carboxyalkyl, dialkylaminoalkyl, hydroxy, amino, acetylamino, propionylamino, aminocarbonyl, alkylaminocarbonyl, dialkylaminocarbonyl, [N-alkyl-N-(dialkylaminoalkyl)amino]carbonyl, [(hydroxycarbonylalkyl)amino]carbonyl, [(alkoxy-carbonylalkyl)amino]carbonyl, (4-morpholinyl) carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, aminocarbonylaminoalkyl, alkylaminocarbonylamino, alkanoyl, cyano, trifluoromethoxy, trifluoromethylthio, trifluoromethylsulfinyl, trifluoromethylsulfonyl, or cycloalkyl groups with 3 to 8 carbon atoms, by 4- to 8-membered alkyleneimino groups wherein a methylene group in the 3-, 4-, or 5-position may be replaced by an oxygen atom or a methylimino group, by alkoxy groups which may be substituted in the co-position by a 5- to 7-membered heteroalicyclic group, where the heteroalicyclic group is linked via a carbon or nitrogen atom and contains one or two heteroatoms not directly connected to each other selected from among oxygen and nitrogen, while multiple substitution by cyclic groups or those groups which contain a carbocyclic or heterocyclic group is excluded and wherein the substituents may be identical or different, and $R^1$ denotes a phenyl, 1-naphthyl, 2-naphthyl, 1,2,3,4-tetrahydro-1-naphthyl, 1H-indol-3-yl, 1-methyl-1H-indol-3-yl, 1-formyl-1H-indol-3-yl, 4-imidazolyl, 1-methyl-4-imidazolyl, 2-thienyl, 3-thienyl, thiazolyl, 1H-indazol-3-yl, 1-methyl-1H-indazol-3-yl, benzo[b]fur-3-yl, benzo[b]thien-3-yl, pyridinyl, quinolinyl, or isoquinolinyl group, whilst the abovementioned aromatic and heteroaromatic groups may additionally be mono-, di-, or trisubstituted in the carbon skeleton by fluorine, chlorine, or bromine atoms, by branched or unbranched alkyl groups, by cycloalkyl groups with 3 to 8 carbon atoms, by phenylalkyl, alkenyl, alkoxy, phenyl, phenylalkoxy, trifluoromethyl, alkoxycarbonylalkyl, carboxyalkyl, alkoxycarbonyl, carboxy, dialkylaminoalkyl, dialkylaminoalkoxy, nitro, hydroxy, amino, acetylamino, propionylamino, methylsulfonyloxy, aminocarbonyl, alkylaminocarbonyl, dialkylaminocarbonyl, alkanoyl, cyano, tetrazolyl, phenyl, pyridinyl, thiazolyl, furyl, trifluoromethoxy, trifluoromethylthio, trifluoromethylsulfinyl, or trifluoromethylsulfonyl groups and the substituents may be identical or different, while the hydroxy, amino, indolyl, and imidazolyl groups contained in the abovementioned groups may be substituted by protecting groups familiar from peptide chemistry, preferably with the acetyl, benzyloxycarbonyl, or tert-butyloxycarbonyl group, and all the abovementioned alkyl and alkoxy groups and the alkyl or alkylene moieties present within the other groups specified may contain 1 to 5 carbon atoms, unless otherwise stated.

By the protecting groups mentioned in the preceding definitions are meant the protecting groups familiar from peptide chemistry, especially a phenylalkoxycarbonyl group with 1 to 3 carbon atoms in the alkoxy moiety optionally substituted in the phenyl nucleus by a halogen atom, by a nitro or phenyl group, by one or two methoxy groups, for example, the benzyloxycarbonyl, 2-nitrobenzyloxycarbonyl, 4-nitrobenzyloxycarbonyl, 4-methoxybenzyloxycarbonyl, 2-chlorobenzyloxycarbonyl, 3-chlorobenzyloxycarbonyl, 4-chlorobenzyloxycarbonyl, 4-biphenylyl-α,α-dimethylbenzyloxycarbonyl, or 3,5-dimethoxy-α,α-dimethylbenzyloxycarbonyl group, an alkoxycarbonyl group having a total of 1 to 5 carbon atoms in the alkyl moiety, for example, the methoxycarbonyl, ethoxycarbonyl, n-propoxycarbonyl, isopropoxycarbonyl, n-butoxycarbonyl, 1-methylpropoxycarbonyl, 2-methylpropoxycarbonyl, or tert-butyloxycarbonyl group, the allyloxycarbonyl, 2,2,2-trichloro-(1,1-dimethylethoxy)carbonyl, or 9-fluorenylmethoxycarbonyl group, or the formyl, acetyl, or trifluoroacetyl group.

The present invention also includes the individual diastereomeric pairs of antipodes of general formula (I), the associated enantiomers and mixtures of the diastereomers and enantiomers which come under general formula (I).

Particularly preferred are the racemates and enantiomers which come under general formula (I) and are trans-configured in relation to the cyclopropane ring.

The compounds of general formula (I) have valuable pharmacological properties, based on their selective CGRP-antagonistic properties. The invention further relates to pharmaceutical compositions containing these compounds, their use, and the preparation thereof.

Preferred compounds of the above general formula (I) are those wherein

R denotes a mono- or diunsaturated 5- to 7-membered aza, diaza, triaza, or thiaza heterocyclic group, whilst the abovementioned heterocyclic groups are linked via a carbon or nitrogen atom, and may contain one or two carbonyl groups adjacent to a nitrogen atom, may be substituted at a carbon atom by a phenyl, pyridinyl, diazinyl, thienyl, pyrrolyl, 1,3-thiazolyl, isoxazolyl, pyrazolyl, or 1-methylpyrazolyl group, and wherein an olefinic double bond of one of the abovementioned unsaturated heterocyclic groups may be fused to a benzene, pyridine, diazine, or quinoline ring, while the phenyl, pyridinyl, diazinyl, thienyl, pyrrolyl, 1,3-thiazolyl, isoxazolyl, pyrazolyl, or 1-methylpyrazolyl groups contained in R and the benzo-, pyrido-, and diazino-fused heterocyclic groups in the carbon skeleton may additionally be mono-, di-, or trisubstituted by fluorine, chlorine, or bromine atoms, by alkyl, dialkylaminoalkoxy, nitro, trifluoromethyl, alkoxycarbonyl, alkoxycarbonylalkyl, alkoxycarbonylalkoxy, hydroxycarbonylalkoxy, carboxy, carboxyalkyl, dialkylaminoalkyl, hydroxy, amino, acetylamino, propionylamino, aminocarbonyl, alkylaminocarbonyl, dialkylaminocarbonyl, [N-alkyl-N-(dialkylaminoalkyl)amino]carbonyl, [(hydroxycarbonylalkyl)amino]carbonyl, [(alkoxycarbonylalkyl)amino]carbonyl, aminocarbonylamino, aminocarbonylaminoalkyl, alkylaminocarbonylamino, alkanoyl, or trifluoromethoxy groups, by 5- to 7-membered alkyleneimino groups wherein a methylene group in the 3-, 4-, or 5-position may be replaced by an oxygen atom or a methylimino group, by alkoxy groups which may be substituted in the ω-position by a 5- to 7-membered heteroalicyclic group, where the heteroalicyclic group is linked via a carbon or nitrogen atom and contains one or two heteroatoms not directly connected to each other selected from among oxygen and nitrogen, while multiple substitution by cyclic groups or those groups which contain a carbocyclic or heterocyclic group is ruled out and wherein the substituents may be identical or different, and $R^1$ denotes a phenyl, 1-naphthyl, or 2-naphthyl group, while the abovementioned aromatic groups may be mono-, di-, or trisubstituted by fluorine, chlorine, or bromine atoms, by branched or unbranched alkyl groups, alkoxy, trifluoromethyl, nitro, hydroxy, amino, or acetylamino groups and the substituents may be identical or different, and wherein all the abovementioned alkyl and alkoxy groups and the alkyl or alkylene moieties present within the other groups mentioned may contain 1 to 4 carbon atoms, unless otherwise stated, the tautomers, diastereomers, enantiomers, and salts thereof.

Particularly preferred compounds of the above general formula (I) are those wherein R denotes a monounsaturated 5- to 7-membered diaza or triaza heterocyclic group, while the abovementioned heterocyclic groups are linked via a nitrogen atom, may contain a carbonyl group adjacent to a nitrogen atom, and may be substituted at a carbon atom by a phenyl group, or an olefinic double bond of one of the abovementioned unsaturated heterocyclic groups may be fused with a benzene, pyridine, or quinoline ring, and the phenyl groups contained in R as well as the benzo- and pyrido-fused heterocyclic groups in the carbon skeleton may additionally be mono-, di-, or trisubstituted by fluorine, chlorine, or bromine atoms, by alkyl, dialkylaminoalkoxy, nitro, trifluoromethyl, alkoxycarbonyl, alkoxycarbonylalkoxy, hydroxycarbonylalkoxy, carboxy, hydroxy, aminocarbonyl, alkylaminocarbonyl, dialkylaminocarbonyl, [N-alkyl-N-(dialkylaminoalkyl)-amino]carbonyl, [(hydroxycarbonylalkyl)amino]carbonyl, [(alkoxycarbonylalkyl)amino]carbonyl, alkanoyl, or trifluoromethoxy groups, by 5- to 7-membered alkyleneimino groups wherein a methylene group in the 3- or 4-position may be replaced by an oxygen atom or a methylimino group, for example, 1-pyrrolidinyl, 1-piperidinyl, 4-methyl-1-piperazinyl, 4-methyl-1,4-diazacyclohept-1-yl, or 4-morpholinyl groups, by alkoxy groups which may be substituted in the co-position by a 5- or 6-membered heteroalicyclic group, wherein the heteroalicyclic group is linked via a carbon atom and contains an oxygen atom in each of the 2- and 2'-positions or is linked via a carbon or nitrogen atom and contains one or two nitrogen atoms not directly linked to one another or an oxygen and a nitrogen atom which are separated from each other by at least one methylene group, for example, methoxy, ethoxy, propoxy, 2,5-dioxacyclopentylmethoxy, 2,6-dioxacyclohexylmethoxy, 2-(1-pyrrolidinyl)ethoxy, 2-(1-piperidinyl)ethoxy, 2-(4-methyl-1-piperazinyl)ethoxy, or 2-(4-morpholinyl)ethoxy groups, while multiple substitution by cyclic groups or those groups which contain a carbocyclic or heterocyclic group is excluded and wherein the substituents may be identical or different, and $R^1$ denotes a phenyl group which may be mono-, di-, or trisubstituted by fluorine, chlorine, or bromine atoms, by alkoxy, trifluoromethyl, nitro, hydroxy, or amino groups, while the substituents may be identical or different, and wherein all the abovementioned alkyl and alkoxy groups and the alkyl or alkylene moieties present within the other groups mentioned may contain 1 to 3 carbon atoms, unless otherwise stated, the tautomers, diastereomers, enantiomers, and salts thereof.

Most particularly preferred compounds of the above general formula (I) are those wherein R denotes a 3,4-dihydro-2(1H)-oxoquinazolin-3-yl, 1,3-dihydro-4-phenyl-2H-2-oxoimidazol-1-yl, 2,4-dihydro-5-phenyl-3 (3H)-oxo-1,2,4-triazol-2-yl, 3,4-dihydro-2(1H)-oxopyrido[4,3-d]pyrimidin-3-yl, 3,4-dihydro-2(1H)- oxopyrido[3,4-d]pyrimidin-3-yl, or 1,3-dihydro-2 (2H)-oxoimidazo[4,5-c]quinolin-3-yl group, wherein the abovementioned mono- and bicyclic heterocyclic groups may be mono- or disubstituted in the carbon skeleton by fluorine, chlorine, or bromine atoms or may be monosubstituted by a 4-methyl-1-piperazinyl, 2,5-dioxacyclopentylmethoxy, methoxy, 2-(4-morpholinyl)ethoxy, 2-dimethylaminoethoxy, 3-dimethylaminopropoxy, methoxycarbonylmethoxy, hydroxycarbonylmethoxy, nitro, trifluoromethyl, methoxycarbonyl, carboxy, hydroxy, aminocarbonyl, diethylaminocarbonyl, [N-(2-dimethylaminoethyl)-N-methylamino]carbonyl, [(methoxycarbonylmethyl)amino]carbonyl, or [(hydroxycarbonylmethyl)amino]carbonyl group, and $R^1$ denotes a phenyl group, which may be mono-, di-, or trisubstituted by fluorine, chlorine, or bromine atoms or by hydroxy or amino groups, wherein the substituents may be identical or different, for example, the 4-chlorophenyl, 4-amino-3,5-dibromophenyl, or 3,5-dibromo-4-hydroxyphenyl group, the tautomers, diastereomers, enantiomers, and salts thereof.

The following are mentioned as examples of particularly preferred compounds:

(1) cis-3-{1-[2-(4-chlorobenzoyl)cyclopropanecarbonyl]-4-piperidinyl}-3,4-dihydro-2(1H)-quinazolinone;

(2) trans-1-{1-[2-(4-amino-3,5-dibromobenzoyl)cyclopropanecarbonyl]-4-piperidinyl}-1,3-dihydro-4-(3-methoxyphenyl)-2 (2H)-imidazolone;

(3) trans-3-{1-[2-(4-amino-3,5-dibromobenzoyl)cyclopropanecarbonyl]-4-piperidinyl}-3,4-dihydro-2(1H)-quinazolinone;

(4) trans-3-{1-[2-(4-amino-3,5-dibromobenzoyl)cyclopropanecarbonyl]-4-piperidinyl}-6-bromo-3,4-dihydro-2 (1H)-quinazolinone;

(5) trans-1-{1-[2-(4-amino-3,5-dibromobenzoyl)cyclopropanecarbonyl]-4-piperidinyl}-1,3-dihydro-4-phenyl-2 (2H)-imidazolone;

(6) trans-1-{1-[2-(4-amino-3,5-dibromobenzoyl)cyclopropanecarbonyl]4-piperidinyl}-1,3-dihydro-4-[3-(trifluoromethyl)phenyl]-2(2H)-imidazolone;

(7) trans-1-{1-[2-(4-amino-3,5-dibromobenzoyl)cyclopropanecarbonyl]-4-piperidinyl}-1,3-dihydro-4-(3-hydroxyphenyl)-2(2H)-imidazolone;

(8) trans-3-{1-[2-(4-amino-3,5-dibromobenzoyl)cyclopropanecarbonyl]-4-piperidinyl}-3,4-dihydro-6-hydroxy-2 (1H)-quinazolinone;

(9) trans-3-{1-[2-(4-amino-3,5-dibromobenzoyl)cyclopropanecarbonyl]-4-piperidinyl}-3,4-dihydro-6-[(1,3-dioxolan-2-yl)methoxy]-2(1H)-quinazolinone;

(10) trans-1-{1-[2-(4-amino-3,5-dibromobenzoyl)cyclopropanecarbonyl]-4-piperidinyl}-4-(3,4-dichlorophenyl)-1,3-dihydro-2(2H)-imidazolone;

(11) trans-3-{1-[2-(4-amino-3,5-dibromobenzoyl)cyclopropanecarbonyl]-4-piperidinyl}-3,4-dihydro-2(1H)-pyrido[4,3-d]pyrimidinone;

(12) trans-1-{1-[2-(4-amino-3,5-dibromobenzoyl)cyclopropanecarbonyl]-4-piperidinyl}-1,3-dihydro-4-(2-methoxyphenyl)-2(2H)-imidazolone;

(13) trans-1-{1-[2-(4-amino-3,5-dibromobenzoyl)cyclopropanecarbonyl]-4-piperidinyl}-4-(3-chlorophenyl)-1,3-dihydro-2(2H)-imidazolone;

(14) trans-1-{1-[2-(4-amino-3,5-dibromobenzoyl)cyclopropanecarbonyl]-4-piperidinyl}-1,3-dihydro-4-(3-nitrophenyl)-2(2H)-imidazolone;

(15) trans-3-{1-[2-(4-amino-3,5-dibromobenzoyl)cyclopropanecarbonyl]-4-piperidinyl}-3,4-dihydro-2(1H)-pyrido[3,4-d]pyrimidinone;

(16) trans-3-{1-[2-(4-amino-3,5-dibromobenzoyl)cyclopropanecarbonyl]-4-piperidinyl}-3,4-dihydro-6-[2-(dimethylamino)ethoxy]-2(1H)-quinazolinone;

(17) trans-3-{1-[2-(4-amino-3,5-dibromobenzoyl)cyclopropanecarbonyl]-4-piperidinyl}-3,4-dihydro-6-(4-methyl-1-piperazinyl)-2(1H)-quinazolinone;

(18) trans-1-{1-[2-(4-amino-3,5-dibromobenzoyl)cyclopropanecarbonyl]-4-piperidinyl}-1,3-dihydro-4-[2-(trifluoromethyl)phenyl]-2(2H)-imidazolone;

(19) trans-3-{1-[2-(4-amino-3,5-dibromobenzoyl)cyclopropanecarbonyl]-4-piperidinyl}-3,4-dihydro-6-[3-(dimethylamino)propoxy]-2(1H)-quinazolinone;

(20) trans-3-{1-[2-(3,5-dibromo-4-hydroxybenzoyl)cyclopropanecarbonyl]-4-piperidinyl}-3,4-dihydro-2(1H)-quinazolinone;

(21) trans-1-{1-[2-(3,5-dibromo-4-hydroxybenzoyl)cyclopropanecarbonyl]-4-piperidinyl}-1,3-dihydro-4-phenyl-2 (2H)-imidazolone;

(22) trans-3-{1-[2-(4-amino-3,5-dibromobenzoyl)cyclopropanecarbonyl]-4-piperidinyl}-3,4-dihydro-6-(methoxycarbonylmethoxy)-2(1H)-quinazolinone;

(23) trans-3-{1-[2-(4-amino-3,5-dibromobenzoyl)cyclopropanecarbonyl]-4-piperidinyl}-3,4-dihydro-6-(hydroxycarbonylmethoxy)-2(1H)-quinazolinone;

(24) trans-3-{1-[2-(4-amino-3,5-dibromobenzoyl)cyclopropanecarbonyl]-4-piperidinyl}-3,4-dihydro-6-[2-(4-morpholinyl)ethoxy]-2(1H)-quinazolinone;

(25) trans-3-{1-[2-(4-amino-3,5-dibromobenzoyl)cyclopropanecarbonyl]-4-piperidinyl}-3,4-dihydro-7-methoxy-2 (1H)-quinazolinone;

(26) trans-3-{1-[2-(4-amino-3,5-dibromobenzoyl)cyclopropanecarbonyl]-4-piperidinyl}-3,4-dihydro-7-(methoxycarbonylmethoxy)-2(1H)-quinazolinone;

(27) trans-3-{1-[2-(4-amino-3,5-dibromobenzoyl)cyclopropanecarbonyl]-4-piperidinyl}-7-carboxy-3,4-dihydro-2 (1H)-quinazolinone;

(28) trans-3-{1-[2-(4-amino-3,5-dibromobenzoyl)cyclopropanecarbonyl]-4-piperidinyl}-7-methoxycarbonyl-3,4-dihydro-2(1H)-quinazolinone;

(29) trans-3-{1-[2-(4-amino-3,5-dibromobenzoyl)cyclopropanecarbonyl]-4-piperidinyl}-1,3-dihydro-2(2H)-imidazo[4,5-c]quinolinone;

(30) trans-3-{1-[2-(4-amino-3,5-dibromobenzoyl)cyclopropanecarbonyl]-4-piperidinyl}-3,4-dihydro-7-{[(methoxycarbonylmethyl)amino]carbonyl}-2(1H)-quinazolinone;

(31) trans-3-{1-[2-(4-amino-3,5-dibromobenzoyl)cyclopropanecarbonyl]-4-piperidinyl}-3,4-dihydro-7-{[N-(2-dimethylaminoethyl)-N-methylamino]carbonyl}-2(1H)-quinazolinone;

(32) trans-3-{1-[2-(4-amino-3,5-dibromobenzoyl)cyclopropanecarbonyl]-4-piperidinyl}-7-diethylaminocarbonyl-3,4-dihydro-2(1H)-quinazolinone;

(33) trans-7-aminocarbonyl-3-{1-[2-(4-amino-3,5-dibromobenzoyl)cyclopropanecarbonyl]-4-piperidinyl}-3,4-dihydro-2(1H)-quinazolinone;

(34) trans-3-{1-[2-(4-amino-3,5-dibromobenzoyl)cyclopropanecarbonyl]-4-piperidinyl}-3,4-dihydro-7-{[(hydroxycarbonylmethyl)amino]carbonyl}-2(1H)-quinazolinone; and

(35) trans-1-{1-[2-(4-amino-3,5-dibromobenzoyl)cyclopropanecarbonyl]-4-piperidinyl}-2,4-dihydro-5-phenyl-3 (3H)-1,2,4-triazolone, particularly compounds (2), (3), (5), (7), (8), (9), (13), (19), (22), (23), and (35) mentioned above, and the salts thereof.

The compounds of general formula (I) are prepared by methods known in principle. The following methods have proved particularly suitable for preparing the compounds of general formula (I) according to the invention:

a) Coupling a Carboxylic Acid of General Formula

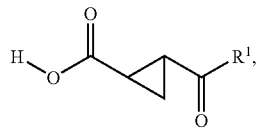

(II)

wherein
R¹ is as hereinbefore defined,
with a compound of general formula

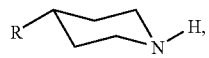

(III)

wherein
R is as hereinbefore defined.

The coupling is preferably carried out using methods known from peptide chemistry (cf., e.g., Houben-Weyl, Methoden der Organischen Chemie, Vol. 15/2), for example, using carbodiimides such as, e.g., dicyclohexylcarbodiimide (DCC), diisopropyl carbodiimide (DIC), or ethyl-(3-dimethylaminopropyl)carbodiimide, or O-(1H-benzotriazol-1-yl)-N,N,N',N'-tetramethyluronium hexafluorophosphate (HBTU), tetrafluoroborate (TBTU), or 1H-benzotriazol-1-yloxy-tris(dimethylamino)phosphonium hexafluorophosphate (BOP). By adding 1-hydroxybenzotriazole (HOBt) or 3-hydroxy-4-oxo-3,4-dihydro-1,2,3-benzotriazine (HOObt), any possible racemization can additionally be suppressed, if desired, or the reaction speed can be increased. The couplings are normally carried out with equimolar amounts of the coupling components as well as the coupling reagent in solvents such as dichloromethane, tetrahydrofuran, acetonitrile, dimethylformamide (DMF), dimethylacetamide (DMA), N-methylpyrrolidone (NMP) or mixtures thereof and at temperatures between −30° C. and +30° C., preferably −20° C. and +25° C. If necessary, N-ethyldiisopropylamine (DIEA) (Hünig base) is preferably used as an additional auxiliary base.

The so-called anhydride process is used as a further coupling method for synthesizing compounds of general formula (I) (cf. also: M. Bodanszky, "Peptide Chemistry", Springer-Verlag 1988, pp. 58-59; M. Bodanszky, "Principles of Peptide Synthesis", Springer-Verlag 1984, pp. 21-27). The Vaughan variant of the mixed anhydride process is preferred (J. R. Vaughan Jr., J. Amer. Chem. Soc. 73, 3547 (1951)), in which the mixed anhydride of the carboxylic acid of general formula (III) which is to be coupled and monoisobutyl carbonate, is obtained using isobutyl chlorocarbonate in the presence of bases such as 4-methylmorpholine or 4-ethylmorpholine. The preparation of this mixed anhydride and the coupling with amines are carried out in a one-pot process, using the abovementioned solvents and at temperatures between −20° C. and +25° C., preferably 0° C. and +25° C.

b) Coupling a Compound of General Formula

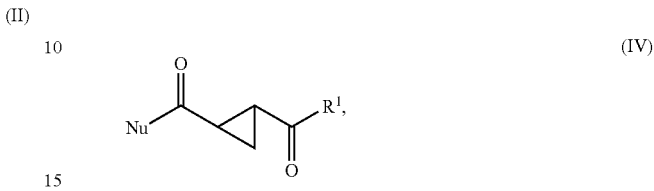

(IV)

wherein
R¹ is as hereinbefore defined, and Nu denotes a leaving group, e.g., a halogen atom such as the chlorine, bromine, or iodine atom, an alkylsulfonyloxy group with 1 to 10 carbon atoms in the alkyl moiety, a phenylsulfonyloxy or naphthylsulfonyloxy group optionally mono-, di-, or trisubstituted by chlorine or bromine atoms, by methyl or nitro groups, whilst the substituents may be identical or different, a 1H-imidazol-1-yl, a 1H-pyrazol-1-yl optionally substituted by 1 or 2 methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl, or pyridinyl, a dimethylaminyloxy, 2(1H)-oxopyridin-1-yloxy, 2,5-dioxopyrrolidin-1-yloxy, phthalimidyloxy, 1H-benzotriazol-1-yloxy, or azide group,
with a compound of general formula

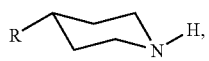

(III)

wherein
R is as hereinbefore defined.

The reaction is carried out under Schotten-Baumann or Einhorn conditions, i.e., the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g., sodium hydroxide, potassium hydroxide, or barium hydroxide, alkali metal carbonates, e.g., sodium carbonate, potassium carbonate, or cesium carbonate, alkali metal acetates, e.g., sodium or potassium acetate, as well as tertiary amines, e.g., pyridine, 2,4,6-trimethylpyridine, quinoline, triethylamine, N-ethyldiisopropylamine, N-ethyldicyclohexylamine, 1,4-diazabicyclo[2,2,2]octane, or 1,8-diazabicyclo[5,4,0]undec-7-ene, the solvents used may be, for example, dichloromethane, tetrahydrofuran, 1,4-dioxane, acetonitrile, dimethylformamide, dimethylacetamide, N-methylpyrrolidone, or mixtures thereof; if alkali metal or alkaline earth metal hydroxides, alkali metal carbonates or acetates are used as the auxiliary bases, water may also be added to the reaction mixture as cosolvent.

c) Cyclopropanization of a Compound of General Formula

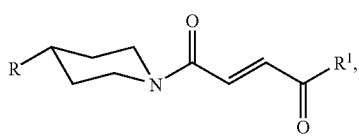

wherein
R and R¹ are as hereinbefore defined.

The cyclopropanization may be carried out catalytically with diazomethane, using starting compounds of formula (V) in which the olefinic double bond is preferably (E)-configured. The reaction is carried out at temperatures between 0° C. and +50° C., preferably at ambient temperature. The preferred catalysts are palladium (II) compounds, for example, $PdCl_2(PhCN)_2$ or palladium (II) acetate, $Pd_3(OAc)_6$. Suitable solvents include inert ethers, for example, diethyl ether, hydrocarbons and most preferably chlorohydrocarbons such as dichloromethane or 1,2-dichloroethane, or mixtures of these solvents (cf. also: H. Abdallah, R. Green, and R. Carrie, Tetrahedron Letters 23, 503-506 (1982)). The cyclopropanization of (E)-configured compounds of general formula (V) can also be made asymmetric by using the semicorrin copper catalysts described by A. Pfaltz, Acc. Chem. Res. 26, 339-345 (1993), thereby obtaining a high enantiomeric excess. The diazomethane required may also be produced in situ, by adding N-methyl-N-nitrosourea batchwise to a mixture of an alkene of general formula (V), the palladium catalyst, the organic solvent, and 40% to 50% aqueous potassium hydroxide solution; with this method, at most 2 moles of N-methyl-N-nitrosourea are generally needed per mol of the alkene of general formula (V).

Moreover, the cyclopropanization of alkenes of general formula (V) wherein the olefinic double bond may be in any orientation, but preferably the (E)-configuration, may be carried out analogously to the so-called Simmons-Smith reaction with diiodomethane and the zinc/copper pair (cf. also: Simmons, Cairns, Vladuchik, and Hoiness, Org. React. 20, 1-131 (1973); Furukawa and Kawabata, Adv. Organomet. Chem. 12, 83-134 (1974)) or the zinc/silver pair (cf. also: J. M. Denis, C. Girard, and J. M. Conia, Synthesis 1972, 549). The zinc/copper pair can be produced by numerous alternative methods (cf., for example, Shank and Shechter, J. Org. Chem. 24, 1525 (1959); LeGoff, J. Org. Chem. 29, 2048 (1964)), of which the heating of zinc powder with copper (I) chloride in diethyl ether and under nitrogen (Rawson and Harrison, J. Org. Chem. 35, 2057 (1970)) is particularly suitable. The reaction also works with non-activated zinc in an ultrasound bath (cf. also: Repič and Vogt, Tetrahedron Letters 23, 2729 (1982); Repič, Lee, and Giger, Org. Prep. Proced. Int. 16, 25 (1984). The species attacking the alkene of general formula (V) is an organozinc compound which occurs as an intermediate, bis-(iodomethyl)-zinc (cf. also: Georg Wittig and Frank Wingler, Chem. Ber. 97, 2146 (1964)) or the adduct $(ICH_2)_2Zn \cdot ZnI_2$ (Blanchard and Simmons, J. Am. Chem. Soc. 86, 1337 (1964)), the solutions of which are sufficiently stable for physicochemical investigations. The cyclopropanization takes place stereospecifically syn. The reactivity of the reagent can be increased by the addition of a Lewis acid, for example, nickel(II) bromide (cf also: H. Kanai et al., Bull. Chem. Soc. Jap. 56, 1025-1029 (1983), Synthesis 1984, 987), while the diiodomethane required can also be produced in situ from dibromomethane and sodium iodide. In another variant of cyclopropanization, the substrate of general formula (V) is reacted with diiodomethane or another dihalomethane and diethylzinc (cf. also: Furukawa, Kawabata and Nishimura, Tetrahedron 24, 53 (1968), Tetrahedron Letters 1968, 3495; Nishimura, Kawabata, and Furukawa, Tetrahedron 25, 2647 (1969); Miyano and Hashimoto, Bull. Chem. Soc. Jpn. 46, 892 (1973); Friedrich and Biresaw, J. Org. Chem. 47, 1615 (1982)). Finally, the reagent required may also be produced from dihalomethanes and copper (Kawabata, Kamemura, and Naka, J. Am. Chem. Soc. 101, 2139 (1979); Kawabata, Tanimoto, and Fujiwara, Tetrahedron 35, 1919 (1979)). The cyclopropanization is carried out at temperatures between 0° C. and +70° C., preferably at ambient temperature, and using ethereal solvents, for example, diethyl ether or tetrahydrofuran.

The cyclopropanization of an alkene of general formula (V) in which the olefinic double bond may have any desired orientation, but is preferably in the (E)-configuration, may also be carried out with the dimethyloxosulfonium methylide of formula

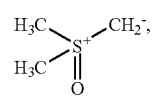

or a dialkylamino-oxosulfonium methylide of general formula

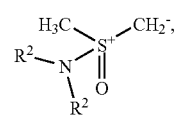

wherein
R² denotes the methyl or ethyl group.

The reaction is carried out in dipolar aprotic solvents, preferably in dimethylsulfoxide, and at temperatures between +10° C. and +80° C., preferably +20° C. and +60° C. The oxosulfonium ylides VI and VII may be put in as such but are also produced in situ from the trimethyloxosulfonium iodide of formula

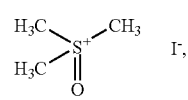

by the action of methanesulfinylmethyl sodium (cf. also: E. J. Corey and M. Chaykowsky, J. Am. Chem. Soc. 87, 1353 (1965), Org. Syn. 49, 78 (1969); H. Schmidbauer and W. Tronich, Tetrahedron Letters 1968, 5335) or from a dialkylamino-oxosulfonium iodide of general formula

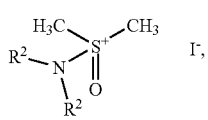

(IX)

wherein
R² is as hereinbefore defined, by the action of sodium hydride (cf. also: C. R. Johnson, E. R. Janiga, and M. Haake, J. Am. Chem. Soc. 90, 3890 (1968); C. R. Johnson and C. W. Schroeck, J. Am. Chem. Soc. 90, 6852 (1968); C. R. Johnson and G. F. Katekar, J. Am. Chem. Soc. 92, 5753 (1970); C. R. Johnson, M. Haake, and C. W. Schroeck, J. Am. Chem. Soc. 92, 6594 (1970); C. R. Johnson and P. E. Rogers, J. Org. Chem. 38, 1793 (1973) in dimethylsulfoxide. Ylides of general formula (VII) can also be obtained in optically active form and are thus suitable for the asymmetric synthesis of compounds of general formula (I).

d) In order to prepare a compound of general formula (I) wherein at least one of the groups R and R¹ contains one or more carboxy groups:
alkaline saponification of a carboxylic acid ester of general formula (Ia)

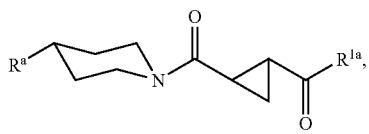

(Ia)

wherein $R^a$ and $R^{1a}$ have the meanings given above for R and R¹, respectively, with the proviso that at least one of these groups contains one or more alkoxycarbonyl groups,
and if desired subsequent treatment with dilute organic or inorganic acids in order to liberate the basic carboxylic acids from the salts initially formed.

For the alkaline saponification of the esters of general formula (Ia), lithium hydroxide, sodium hydroxide, and potassium hydroxide are preferred; however, other alkali metal hydroxides such as cesium hydroxide, or alkaline earth metal hydroxides, for example, barium hydroxide, or tetraalkylammonium hydroxides are also suitable. The procedure is carried out in aqueous solution and advantageously with the addition of water-miscible co-solvents, preferably alcohols such as methanol, ethanol or 2-ethoxyethanol, or ethers such as tetrahydrofuran or 1,4-dioxane. Suitable temperatures for alkaline saponification are between −10° C. and the boiling temperature of the water/solvent mixture used, but ambient temperature is preferred. Dilute aqueous organic or inorganic acids, e.g., acetic acid, oxalic acid, methanesulfonic acid, hydrochloric acid, sulfuric acid, and phosphoric acid are suitable for liberating the basic carboxylic acids from the salts thereof initially formed.

e) In order to prepare a compound of general formula (I) wherein the group R in the carbon skeleton is similarly mono-, di-, or trisubstituted by an aminocarbonyl, alkylaminocarbonyl, dialkylaminocarbonyl, [N-alkyl-N-(dialkylaminoalkyl)amino]carbonyl, hydroxycarbonylalkylaminocarbonyl, alkoxycarbonylalkylaminocarbonyl, (4-morpholinyl)carbonyl, (1-pyrrolidinyl)carbonyl, (1-piperidinyl)carbonyl, (hexahydro-1-azepinyl)carbonyl, or (4-methyl-1-piperazinyl)carbonyl group:

Coupling a compound of general formula

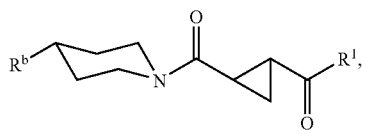

(Ib)

wherein
R¹ is as hereinbefore defined, and the group $R^b$ has the meanings given for R hereinbefore, with the proviso that it is mono-, di-, or trisubstituted in the carbon skeleton by the carboxy group,
with ammonia, alkylamines, N-alkyl-N-(dialkylaminoalkyl) amines, hydroxycarbonylalkylamines, alkoxycarbonylalkylamines, or dialkylamines, for example, 1-methylpiperazine, morpholine, pyrrolidine, piperidine, or hexahydroazepine.

The coupling is preferably carried out using methods known from peptide chemistry (cf., e.g., Houben-Weyl, Methoden der Organischen Chemie, Vol. 15/2), for example, using carbodiimides such as, e.g., dicyclohexylcarbodiimide (DCC), diisopropyl carbodiimide (DIC), or ethyl-(3-dimethylaminopropyl)carbodiimide, or O-(1H-benzotriazol-1-yl)-N,N,N',N'-tetramethyluronium hexafluorophosphate (HBTU), tetrafluoroborate (TBTU), or 1H-benzotriazol-1-yl-oxy-tris(dimethylamino)phosphonium hexafluorophosphate (BOP). By adding 1-hydroxybenzotriazole (HOBt) or 3-hydroxy-4-oxo-3,4-dihydro-1,2,3-benzotriazine (HOObt), any possible racemization can additionally be suppressed, if desired, or the reaction speed can be increased. The couplings are normally carried out with equimolar amounts of the coupling components as well as the coupling reagent in solvents such as dichloromethane, tetrahydrofuran, acetonitrile, dimethylformamide (DMF), dimethylacetamide (DMA), N-methylpyrrolidone (NWP) or mixtures thereof and at temperatures between −30° C. and +30° C., preferably −20° C. and +25° C. If necessary, N-ethyldiisopropylamine (DIEA) (Hünig base) is preferably used as an additional auxiliary base.

The so-called anhydride process is used as a further coupling method for synthesizing compounds of general formula (I) (see also: M. Bodanszky, "Peptide Chemistry", Springer-Verlag 1988, pp. 58-59; M. Bodanszky, "Principles of Peptide Synthesis", Springer-Verlag 1984, pp. 21-27). The Vaughan variant of the mixed anhydride process is preferred (J. R. Vaughan Jr., J. Amer. Chem. Soc. 73, 3547 (1951)), in which the mixed anhydride of the carboxylic acid of general formula (III) which is to be coupled and monoisobutyl carbonate, is obtained using isobutyl chlorocarbonate in the presence of bases such as 4-methylmorpholine or 4-ethylmorpholine. The preparation of this mixed anhydride and the coupling with amines are carried out in a one-pot process, using the abovementioned solvents and at temperatures between −20° C. and +25° C., preferably 0° C. and +25° C.

The new cyclopropanes of general formula (I) according to the invention contain at least one chiral centre. Occasionally, the compounds may occur in the form of two diastereomeric pairs of antipodes. The invention includes the individual isomers and the mixtures thereof.

The diastereomers may be separated on the basis of their different physico-chemical properties, e.g., by fractional crystallization from suitable solvents, by high pressure liquid or column chromatography, using chiral or preferably non-chiral stationary phases.

Racemates covered by general formula (I) may be separated, for example, by HPLC on suitable chiral stationary phases (e.g., Chiral AGP, Chiralpak AD). Racemates which contain a basic or acidic function can also be separated via the diastereomeric, optically active salts which are produced on reacting with an optically active acid, for example, (+)- or (−)-tartaric acid, (+)- or (−)-diacetyl tartaric acid, (+)- or (−)-monomethyl tartrate, or (+)-camphorsulfonic acid, or an optically active base, for example, with (R)-(+)-1-phenylethylamine, (S)-(−)-1-phenylethylamine, or (S)-brucine.

According to a conventional method of separating isomers, the racemate of a compound of general formula (I) is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol, or mixtures thereof, for example, in a ratio by volume of 50:50, are used. Then each of the optically active salts is dissolved in water, neutralized with a base such as sodium carbonate, potassium carbonate, sodium hydroxide solution, or potassium hydroxide solution and in this way the corresponding free compound is obtained in the (+) or (−) form.

The (R) or (S) enantiomer alone or a mixture of two optically active diastereomeric compounds covered by general formula (I) may also be obtained by performing the syntheses described above with a suitable reaction component in the (R) or (S) configuration.

The starting compounds of general formula (Ia) and (Ib) may be prepared by methods a) to c) described in this application. The starting materials of general formula (II) required for the synthesis of the compounds of general formula (I), if not already known from the literature, may easily be prepared, for example, from the corresponding carboxylic acid esters, such as the methyl or ethyl esters, by saponification with aqueous lithium, sodium, or potassium hydroxide solution followed by acidification with hydrochloric acid analogously to methods known in the art. The carboxylates required for this may be obtained from the corresponding 4-aryl- or hetaryl-4-oxo-2-butenoates, for example, by reacting with dimethyloxosulfonium methylide analogously to the process described in c) above. Finally, 4-aryl- or hetaryl-4-oxo-2-butenoates are either known from the literature or may easily be obtained from 4-aryl- or hetaryl-4-oxo-2-butenoic acids known from the literature (cf. also published German applications 2 047 806 and 2 103 749).

Secondary amines of general formula (II) are either known or may be synthesized, for example, analogously to processes described in WO 98/11128.

Starting compounds of general formula (IV) may be obtained from the starting compounds of general formula (II) by current methods.

The starting compounds of general formula (V) may easily be prepared, for example, by acylating compounds of formula (III) with unsaturated carboxylic acid derivatives.

The compounds of general formula (I) obtained may, if they contain suitable basic functions, be converted, particularly for pharmaceutical use, into their physiologically acceptable salts with inorganic or organic acids. Suitable acids include, for example, hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid, or maleic acid.

Moreover, the new compounds of formula (I), if they contain an acid function, for example, a carboxy group, may if desired be converted into the addition salts thereof with inorganic or organic bases, particularly for pharmaceutical use into the physiologically acceptable addition salts thereof. Suitable bases for this include, for example, sodium hydroxide, potassium hydroxide, ammonia, cyclohexylamine, dicyclohexylamine, ethanolamine, diethanolamine, and triethanolamine.

The new compounds of general formula (I) and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of compounds of general formula (I) for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer, mixed with 0.02% EDTA, then detached again and isolated by centrifuging. After resuspension in 20 mL of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40], the cells are centrifuged twice at 100×g and resuspended in BSS. After the number of cells has been determined, the cells are homogenized using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40), enriched with 1% bovine serum albumin and 0.1% bacitracin) and resuspended (1 mL/1000000 cells). The homogenized product is frozen at −80° C. The membrane preparations are stable for more than 6 weeks under these conditions.

After thawing, the homogenized product is diluted 1:10 with assay buffer (50 mM Tris, 150 mM NaCl, 5 mM MgCl$_2$, 1 mM EDTA, pH 7.40) and homogenized for 30 seconds with an Ultra-Turrax. 230 µL of the homogenized product are incubated for 180 minutes at ambient temperature with 50 pM $^{125}$I-iodotyrosyl-Calcitonin-Gene-Related Peptide (Amersham) and increasing concentrations of the test substances in a total volume of 250 µL. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity in the presence of 1 µM human CGRP-alpha during incubation.

The concentration binding curves are analyzed using computer-aided non-linear curve matching.

The compounds of general formula (I) show IC$_{50}$ values ≦10000 nM in the test described.

B. CGRP Antagonism in SK-N-MC Cells

SK-N-MC cells (1 million cells) are washed twice with 250 µl incubation buffer (Hanks' HEPES, 1 mM 3-isobutyl-1-methylxanthine, 1% BSA, pH 7.4) and pre-incubated at 37° C. for 15 minutes. After the addition of CGRP (10 µL) as agonist in increasing concentrations (10$^{-11}$ to 10$^{-6}$ M), or additionally the substance in 3 to 4 different concentrations, the mixture is incubated for another 15 minutes.

Intracellular cAMP is then extracted by the addition of 20 µL of 1M HCl and centrifugation (2000×g, 4° C., for 15 minutes). The supernatants are frozen in liquid nitrogen and stored at −20° C.

The cAMP contents of the samples are determined by radioimmunoassay (Amersham) and the $pA_2$ values of antagonistically acting substances are determined graphically.

The compounds of general formula (I) exhibit CGRP-antagonistic properties in the in vitro test model described, in a dosage range of between $10^{-11}$ to $10^{-5}$ M.

In view of their pharmacological properties the compounds of general formula (I) and the salts thereof with physiologically acceptable acids or bases are thus suitable for the acute and prophylactic treatment of headaches, particularly migraine or cluster headaches. Moreover, the compounds of general formula (I) also have a positive effect on the following diseases: non-insulin-dependent diabetes mellitus ("NIDDM"), cardiovascular diseases, morphine tolerance, skin diseases, particularly thermal and radiation-induced skin damage including sunburn, inflammatory diseases, e.g., inflammatory diseases of the joints (arthritis), inflammatory lung diseases, allergic rhinitis, asthma, diseases accompanied by excessive vasodilatation and consequent reduced circulation of blood through the tissues, e.g., shock and sepsis. The symptoms of menopausal hot flushes in oestrogen-deficient women caused by vasodilatation and increased blood flow are favorably affected by the CGRP-antagonists of the present application in a preventive and acute-therapeutic capacity, this therapeutic approach being distinguished from hormone replacement by the absence of side effects. Furthermore, the compounds of general formula (I) have an alleviating effect on pain in general.

The dosage required to achieve a corresponding effect is conveniently 0.001 to 30 mg/kg of body weight, preferably 0.01 to 5 mg/kg of body weight, when administered intravenously or subcutaneously and 0.01 to 50 mg/kg of body weight, preferably 0.1 to 30 mg/kg of body weight when administered orally, nasally, or by inhalation, 1 to 3× a day in each case.

For this, the compounds of general formula (I) prepared according to the invention, optionally combined with other active substances such as, e.g., antiemetics, prokinetics, neuroleptics, antidepressants, neurokinine antagonists, anticonvulsants, histamine-H1 receptor antagonists, antimuscarinics, β-blockers, α-agonists, and α-antagonists, ergot alkaloids, mild analgesics, non-steroidal antiinflammatories, corticosteroids, calcium antagonists, $5-HT_{1D}$ agonists or other anti-migraine agents, together with one or more inert conventional carriers and/or diluents, e.g., with corn starch, lactose, glucose, microcrystalline cellulose, magnesium stearate, polyvinyl pyrrolidone, citric acid, tartaric acid, water, water/ethanol, water/glycerol, water/sorbitol, water/polyethyleneglycol, propyleneglycol, cetylstearyl alcohol, carboxymethylcellulose, or fatty substances such as hard fat or suitable mixtures thereof, may be formulated into conventional galenic preparations such as plain or coated tablets, capsules, powders, suspensions, solutions, metered dose aerosols, or suppositories.

The active substances which may be used for the above-mentioned combinations thus include, for example, meloxicam, ergotamine, dihydroergotamine, metoclopramide, domperidone, diphenhydramine, cyclizine, promethazine, chlorpromazine, dexamethasone, flunarizine, dextropropoxyphene, meperidine, propranolol, nadolol, atenolol, clonidine, indoramine, carbamazepine, phenytoin, valproate, amitriptyline, lidocaine, diltiazem, or sumatriptan and other $5-HT_{1D}$-agonists such as, for example, naratriptan, zolmitriptan, avitriptan, rizatriptan and eletriptan. The dosage of these active substances is expediently 1/5 of the lowest recommended dose to 1/1 of the normally recommended dose, i.e., for example, 20 to 100 mg of sumatriptan.

The invention further relates to the use of the compounds of general formula (I) as valuable adjuvants for the production and purification (by affinity chromatography) of antibodies as well as, after suitable radioactive labeling, for example, by direct labeling with $^{125}I$ or $^{131}I$ or by tritiation of suitable precursors, for example, by replacing halogen atoms with tritium, in RIA and ELISA assays and as a diagnostic or analytical adjuvant in neurotransmitter research.

The Examples which follow are intended to illustrate the invention:

Preliminary Remarks: Satisfactory elementary analyses, IR, UV, $^1$H-NMR, and generally also mass spectra have been obtained for all of the compounds. Unless otherwise stated, $R_f$ values were obtained using ready-made silica gel TLC plates 60 $F_{254}$ (E. Merck, Darmstadt, Item No. 1.05714) without chamber saturation. If no detailed information is given as to the configuration, it is not clear whether it is a pure enantiomer or whether partial or even complete racemization has occurred. The following eluants or mixtures of eluants were used for the chromatography:

El A=ethyl acetate/methanol 100/5 (v/v)
El B=ethyl acetate/methanol 80/20 (v/v)
El C=ethyl acetate/methanol/conc. ammonia 80/20/1 (v/v/v)
El D=dichloromethane/cyclohexane/methanol/conc. ammonia 70/15/15/2 (v/v/v/v)
El E=ethyl acetate/glacial acetic acid 99/1 (v/v)
El F=ethyl acetate/methanol/glacial acetic acid 90/10/1 (v/v/v)
El G=dichloromethane/methanol/conc. ammonia 90/10/1 (v/v/v)
El H=petroleum ether/ethyl acetate 1/1 (v/v)
El I=dichloromethane/methanol/glacial acetic acid 90/10/1.5 (v/v/v)
El K=dichloromethane/isopropanol 9/1 (v/v)
El L=ethyl acetate/methanol 9/1 (v/v)
El M=dichloromethane/methanol/conc. ammonia 75/25/0.5 (v/v/v)
El N=dichloromethane/ethyl acetate 1/1 (v/v)
El O=dichloromethane/methanol 95/5 (v/v)
El P=dichloromethane/ethyl acetate/cyclohexane/methanol/conc. ammonia (60/16/5/5/0.6 v/v/v/v/v)

The following abbreviations are used in the description of the experiments:
Mp.: melting point
(D): (decomposition)
DIEA: N,N-diisopropylethylamine
Boc: (1,1'-dimethylethoxy)carbonyl
TBTU: 2-(1H-benzotriazol-1-yl)-1,1,3,3-tetramethyluronium tetrafluoroborate
HOBt: 1-hydroxybenzotriazole hydrate
CDT: 1,1'-carbonyldi-(1,2,4-triazole)
THF: tetrahydrofuran
DMF: dimethylformamide
EE: ethyl acetate
PE: petroleum ether
LM: solvents
I. No.: Item number The meanings of the symbols consisting of letters and numbers used in the Examples are shown in the following summary:

N1 N2 N3 N4 N5 N6 N7
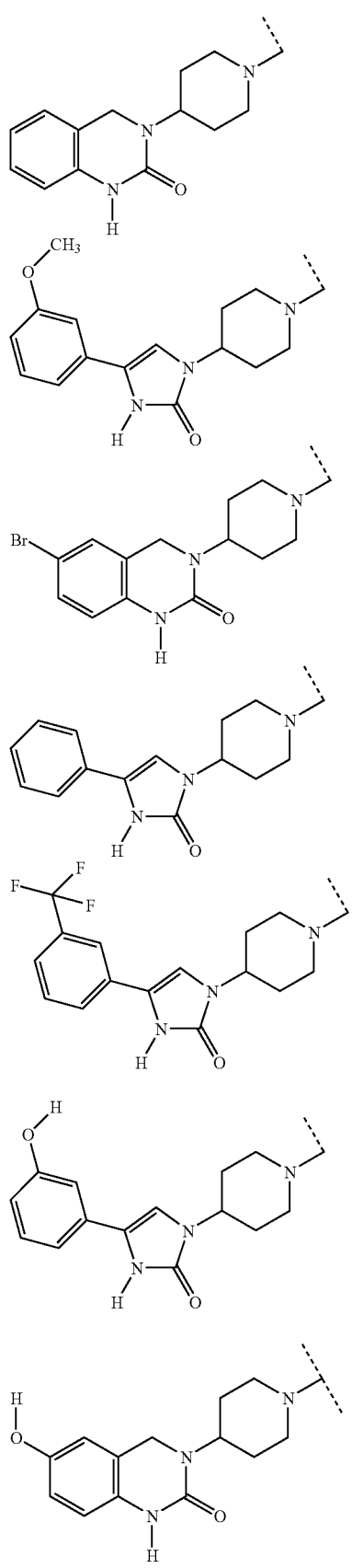
N8 N9 N10 N11 N12 N13
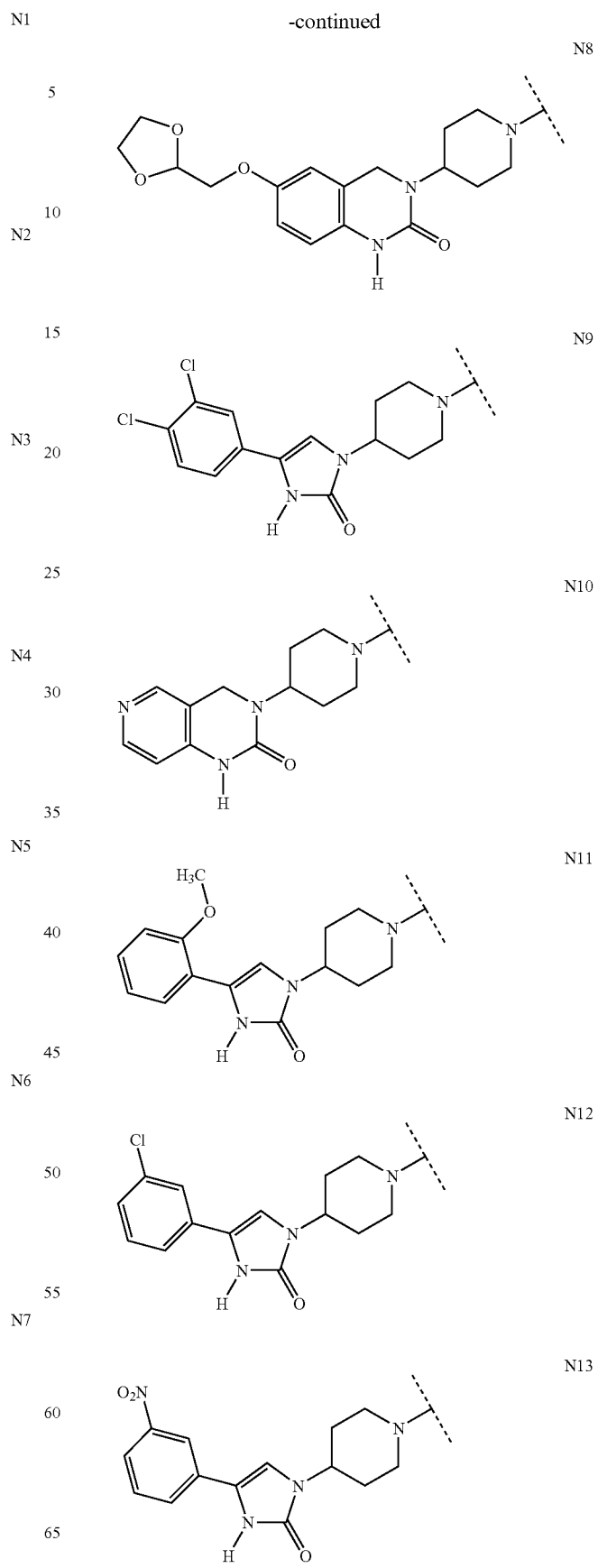

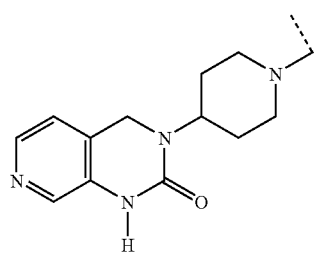 N14
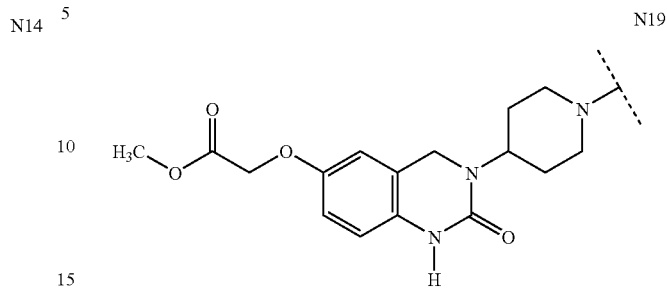 N19
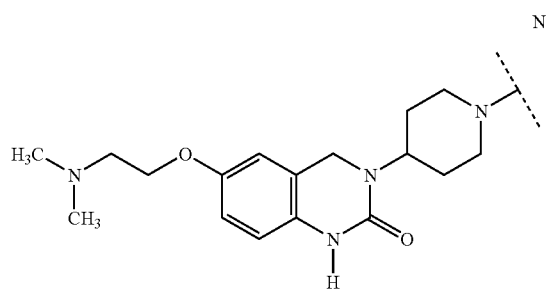 N15
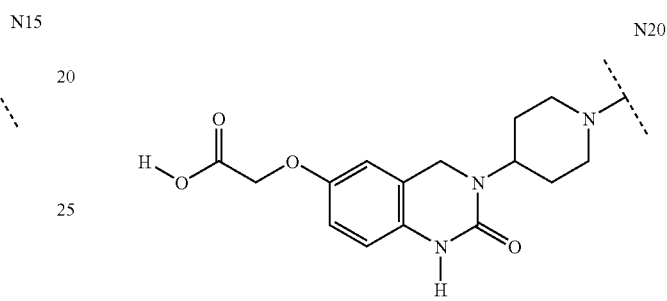 N20
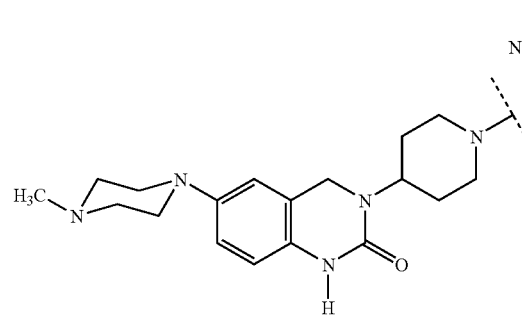 N16
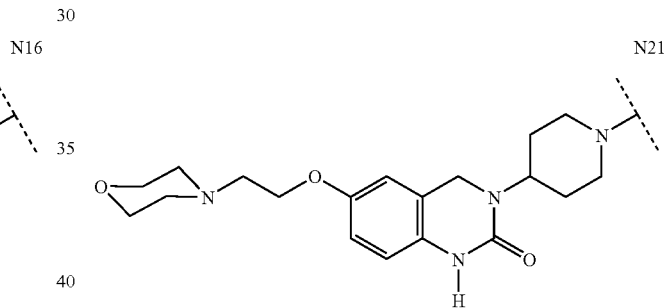 N21
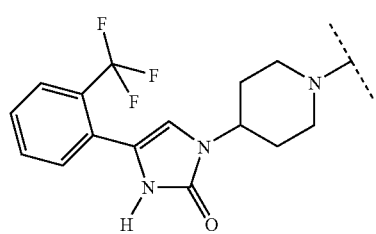 N17
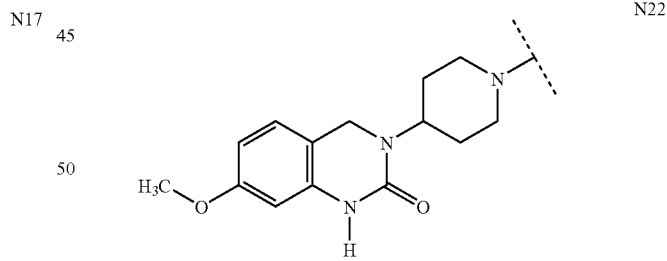 N22
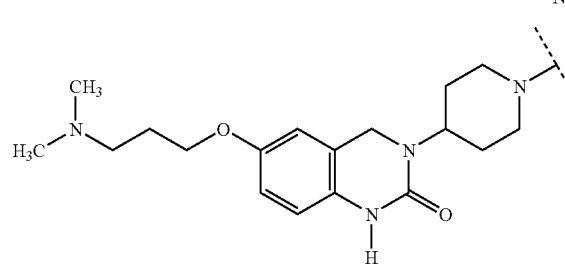 N18
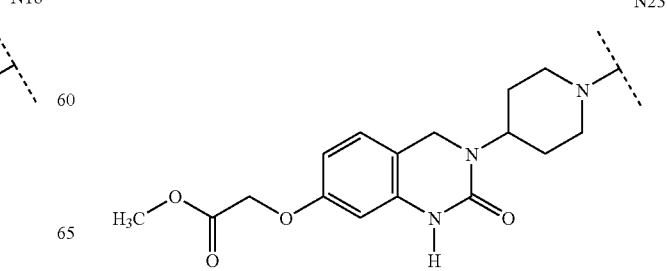 N23

-continued
N24
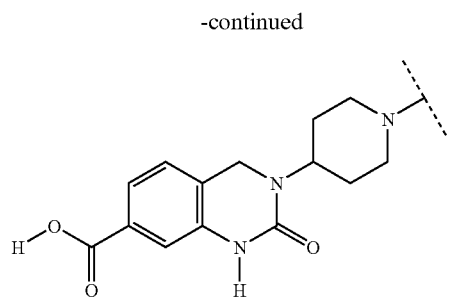
N25
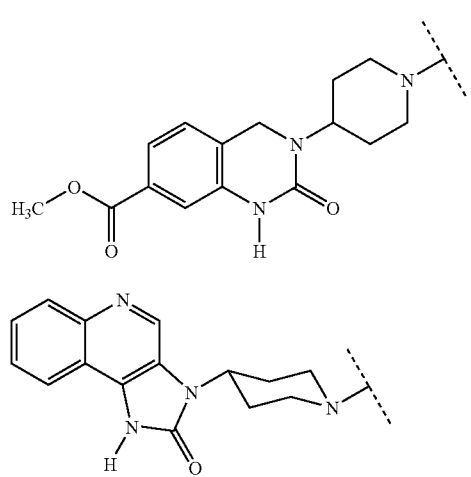
N26
N27
N28
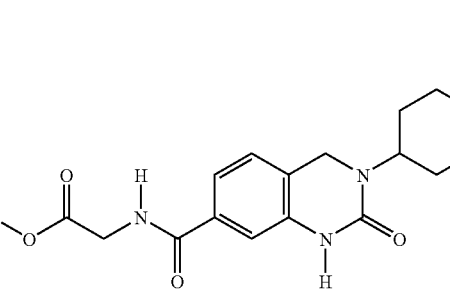
N29
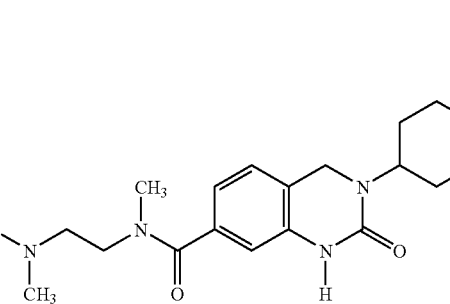
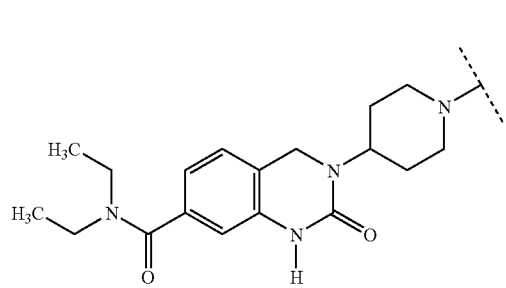
N30
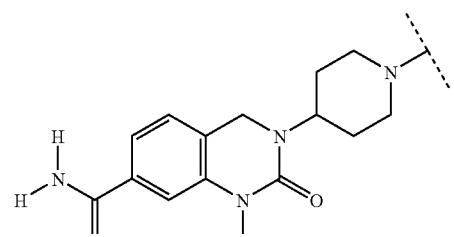
N31
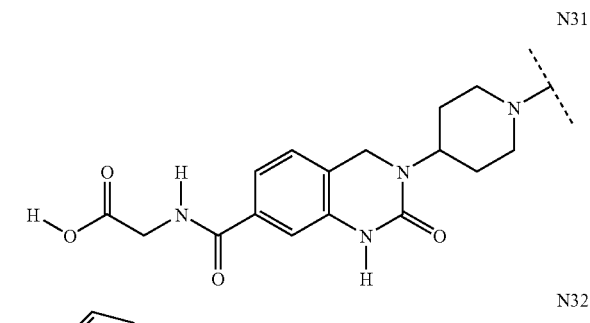
N32
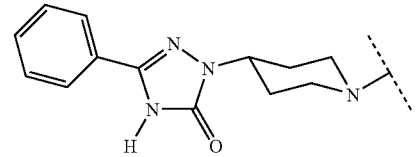
N33
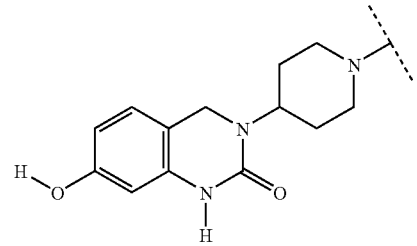
B1
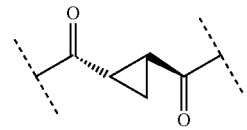
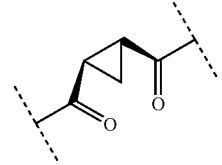
B3
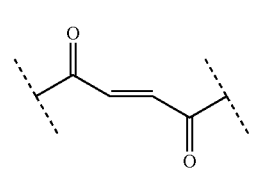

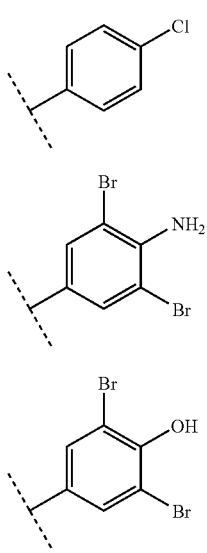

A. Preparation of Intermediate Compounds

EXAMPLE A1 cis-2-(4-chlorobenzoyl)cyclopropanecarboxylic acid 4.5 g (0.040 mol) of chlorobenzene and 5.0 g (0.0446 mol) of 1,2-cyclopropanedicarboxylic acid anhydride were successively added dropwise to a mixture of 60.0 g (0.45 mol) of anhydrous aluminium chloride and 9 mL (0.115 mol) of anhydrous dimethylformamide while maintaining a reaction temperature of 60° C. to 70° C. and the mixture was then kept at 70° C. for 1 hour. After cooling, the reaction mixture was stirred into a mixture of 500 g of crushed ice and 60 mL of concentrated hydrochloric acid, the precipitate was suction filtered, washed thoroughly with water and dried over Siccapent in a vacuum drying chamber at a temperature of 50° C. 7.8 g (87% of theoretical) of colorless crystals were obtained, m.p. 150° C.-153° C.

EXAMPLE A2 trans-2-(4-amino-3,5-dibromobenzoyl)cyclopropanecarboxylic acid

Prepared analogously to Example 2 from methyl trans-2-(4-amino-3,5-dibromobenzoyl)cyclopropanecarboxylate by saponification with lithium hydroxide hydrate in a water-tetrahydrofuran mixture (2/3 v/v) in a yield of 76% of theoretical. Colorless crystals. IR (KBr): 3473.2, 3345.9 (NH$_2$); 1714.4 (C=O) cm$^{-1}$.

EXAMPLE A3 methyl trans-2-(4-amino-3,5-dibromobenzoyl)cyclopropanecarboxylate 0.45 g (0.01781 mol) of 95% sodium hydride was added in small amounts to a solution of 3.9 g (0.02074 mol) of trimethyl-oxosulfonium iodide in 50 mL anhydrous dimethylsulfoxide at ambient temperature, with stirring. The mixture was stirred for another 30 minutes at ambient temperature and then a solution of 5.8 g (0.01598 mol) of methyl trans-4-(4-amino-3,5-dibromophenyl)-4-oxobutenoate in 50 mL of dimethylsulfoxide was added dropwise without external heating, whereupon the temperature of the mixture rose to 35° C., and stirring was continued for another hour at ambient temperature. The mixture was stirred into in 500 mL of saturated aqueous saline solution, then extracted exhaustively with ethyl acetate. The combined ethyl acetate extracts were dried over sodium sulfate and evaporated down in vacuo. The residue yielded 2.6 g (43% of theoretical) of a colorless oil after purification by column chromatography on silica gel (30 to 60 μm) using EE/cyclohexane (1/1 v/v) as eluant. IR (KBr): 3475, 3363 (NH$_2$); 1728, 1662 (C=O) cm$^{-1}$; MS: M$^+$=375/377/379 (Br$_2$).

EXAMPLE A4 methyl trans-4-(4-amino-3,5-dibromophenyl)-4-oxobutenoate

A mixture of 5.6 g (0.016 mol) of trans-4-(4-amino-3,5-dibromophenyl)-4-oxobutenoic acid, 50 mL of anhydrous methanol, and 4.0 g (0.0368 mol) of trimethylchlorosilane was stirred for 3 days at ambient temperature. The solvent was removed in vacuo, the residue was divided between ethyl acetate and 10% sodium hydrogen carbonate solution. The organic phase was dried over sodium sulfate, evaporated down once more in vacuo, and yielded 5.8 g (100% of theoretical) of a colorless oil which was used without any further purification. MS: M$^+$=361/363/365 (Br$_2$).

EXAMPLE A5

3,4-dihydro-6-[2-(dimethylamino)ethoxy]-3-(4-piperidinyl)-2(1H)-quinazolinone

A mixture of 0.9 g (0.0022 mol) of 3,4-dihydro-6-[2-(dimethylamino)ethoxy]-3-(1-phenylmethyl-4-piperidinyl)-2(1H)-quinazolinone, 10 mL methanol, and 0.5 g palladium (II) hydroxide (Pearlman's catalyst) was hydrogenated until the uptake of hydrogen ended. The catalyst was filtered off, the filtrate was evaporated down in vacuo, and the residue remaining was used in the next step without any further purification. Yield: 0.6 g (86% of theoretical). IR (KBr): 1662 (C=O) cm$^{-1}$; MS: M$^+$=318.

The following were obtained accordingly:

| N | B | C | Remarks | % yield | El | R$_f$ | IR [cm$^{-1}$] |
|---|---|---|---------|---------|----|----|------------|
| N8 | H | — | from N8-CH$_2$Ph, H$_2$, 10% Pd—C, MeOH | 92 | D | 0.23 | 1665 (C=O) |
| N18 | H | — | from N18-CH$_2$Ph, H$_2$, Pd(OH)$_2$, MeOH | 81 | D | 0.26 | |
| N19 | H | — | from N19-CH$_2$Ph, H$_2$, Pd(OH)$_2$, MeOH | 85 | | | |
| N21 | H | — | from N21-CH$_2$Ph, H$_2$, Pd(OH)$_2$, MeOH | 100 | D | 0.27 | |
| N23 | H | — | from N23-CH$_2$Ph, H$_2$, Pd(OH)$_2$, MeOH | 74 | D | 0.35 | |

EXAMPLE A6

3,4-dihydro-6-(4-methyl-1-piperazinyl)-3-(4-piperidinyl)-2(1H)-quinazolinone 2 mL of trifluoroacetic acid were added to the ice-cooled solution of 1.1 g (2.561 mmol) of 3,4-dihydro-3-[1-(1,1-dimethylethoxycarbonyl)-4-piperidinyl]-6-(4-methyl-1-piperazinyl)-2(1H)-quinazolinone in 20 mL of methylene chloride. The reaction mixture was stirred for 15 hours at ambient temperature and for 5 hours at 40° C. and then evaporated down in vacuo. The residue remaining was taken up in 5 mL of water, the solution formed was saturated with potassium carbonate and extracted exhaustively with dichloromethane. The combined extracts were evaporated down in vacuo. The residue obtained was purified by column chromatography on silica gel using dichloromethane/methanol 9/1 (v/v) to start with, then dichloromethane/methanol/concentrated ammonia 70/30/3 (v/v/v) as eluant. The appropriate fractions were evaporated down in vacuo, the residue remaining (0.5 g; 59% of theoretical) was used in the next step without further purification.

EXAMPLE A7

3,4-dihydro-6-[(1,3-dioxolan-2-yl)methoxy]-3-(1-phenylmethyl-4-piperidinyl)-2(1H)-quinazolinone 0.36 g (14.25 mmol) of 95% sodium hydride was added batchwise, with stirring, to a solution of 5.0 g (14.82 mmol) of 3,4-dihydro-6-hydroxy-3-(1-phenylmethyl-4-piperidinyl)-2(1H)-quinazolinone in 120 mL of anhydrous dimethylformamide at ambient temperature and the mixture was then kept for 15 minutes at 50° C. A thick, colorless slurry was formed. After the addition of 5.0 g (37.04 mmol) of 2-(bromomethyl)-1,3-dioxolane the mixture was heated to 90° C. for 90 minutes. After cooling, the mixture was stirred into saturated aqueous saline solution and extracted exhaustively with ethyl acetate. The combined extracts were dried over sodium sulfate and evaporated down in vacuo, the residue remaining was purified by column chromatography on silica gel (30-60 μm) using dichloromethane/EE/cyclohexane/methanol/concentrated ammonia 60/16/5/5/0.6 v/v/v/v/v as eluant. Working up the corresponding fractions yielded 2.5 g (41% of theoretical) of a colorless oil, $R_f$=0.47 (dichloromethane/EE/cyclohexane/methanol/concentrated ammonia 60/16/5/5/0.6 v/v/v/v/v). IR (KBr): 1662 (C=O) cm$^{-1}$.

The following were obtained accordingly:

| N | B | C | Remarks | % yield | El | $R_f$ |
|---|---|---|---------|---------|----|----|
| N19 | — | CH$_2$Ph | from N7-CH$_2$Ph, BrCH$_2$CO$_2$CH$_3$ and NaH in DMF | 63 | | |
| N23 | — | CH$_2$Ph | from N33-CH$_2$Ph, BrCH$_2$CO$_2$CH$_3$ and NaH in DMF | 17 | D | 0.74 |

EXAMPLE A8

3,4-dihydro-6-[2-(dimethylamino)ethoxy]-3-(1-phenylmethyl-4-piperidinyl)-2(1H)-quinazolinone A mixture of 1.1 g (3.26 mmol) of 3,4-dihydro-6-hydroxy-3-(1-phenylmethyl-4-piperidinyl)-2(1H)-quinazolinone, 50 mL of tetrahydrofuran, 0.30 g (3.366 mmol) of 2-dimethylaminoethanol, 0.94 g (3.584 mmol) of triphenylphosphine, and 0.56 g (3.216 mmol) of azodicarboxylic acid ester was stirred for one hour at ambient temperature, 6 hours at reflux temperature and another 13 hours at ambient temperature. The solvent was removed in vacuo and the residue was purified by column chromatography on silica gel (30-60 μm) using dichloromethane/EE/cyclohexane/methanol/concentrated ammonia 60/16/5/5/0.6 v/v/v/v/v as eluant. Working up the corresponding fractions yielded 0.9 g (69% of theoretical) of a colorless crystalline substance, $R_f$=0.47 (dichloromethane/EE/cyclohexane/methanol/concentrated ammonia 60/16/5/5/0.6 v/v/v/v/v).

MS: ESI: (M+H)$^+$=409; (M+2H)$^{++}$=205; (M+Na)$^+$=431

The following were obtained accordingly:

| N | B | C | Remarks | % yield | El | $R_f$ | MS | IR [cm$^{-1}$] |
|---|---|---|---------|---------|----|----|----|----|
| N18 | — | CH$_2$Ph | from N7-CH$_2$Ph, (H$_3$C)$_2$NCH$_2$CH$_2$CH$_2$OH, PPh$_3$ and (NCO$_2$Et)$_2$ in THF | 59 | P | 0.12 | M$^+$ = 422 | 3357, 3271 (NH); 1622 (C=O, C=C) |
| N21 | — | CH$_2$Ph | from N7-CH$_2$Ph, O[(H$_2$C)$_2$]$_2$NCH$_2$CH$_2$OH, PPh$_3$ and (NCO$_2$Et)$_2$ in THF | 45 | | | | |

EXAMPLE A9

3,4-dihydro-3-[1-(1,1-dimethylethoxycarbonyl)-4-piperidinyl]-6-(4-methyl-1-piperazinyl)-2(1H)-quinazolinone A mixture of 10.0 g (24.372 mmol) of 6-bromo-3,4-dihydro-3-[1-(1,1-dimethylethoxycarbonyl)-4-piperidinyl]-2(1H)-quinazolinone, 2.5 g (24.96 mol) of 1-methylpiperazine, 4.81 g (50.05 mmol) of sodium tert-butoxide, 285 mg (0.4766 mmol) of bis(dibenzylideneacetone)palladium, 305 mg (1.002 mmol) of tris(o-tolyl)phosphine, and 100 mL of toluene was refluxed for 14 hours. After the addition of further equal amounts of 1-methylpiperazine, sodium tert-butoxide, bis(dibenzylideneacetone)palladium, and tris(o-tolyl)phosphine the mixture was refluxed for another 48 hours. The mixture was filtered through activated charcoal and the filtrate was evaporated down in vacuo. The residue was divided between dichloromethane and water. The organic phase was extracted twice with dilute aqueous citric acid solution. The acidic extracts thus obtained were made alkaline with sodium hydroxide and extracted exhaustively with dichloromethane. The combined dichloromethane extracts were evaporated down in vacuo, the residue was purified by column chromatography on silica gel (30-60 μm) using dichloromethane to start with, then methanol/concentrated ammonia 9/1 v/v as eluant. After conventional working up of the appropriate eluates 1.1 g (11% of theoretical) of a colorless substance was obtained. IR (KBr): 1670 (C=O) cm$^{-1}$; MS: M$^+$=429.

EXAMPLE A10

3,4-dihydro-7-hydroxy-3-(1-phenylmethyl-4-piperidinyl)-2(1H)-quinazolinone

A mixture of 18.0 g (0.0512 mol) of 3,4-dihydro-7-methoxy-3-(1-phenylmethyl-4-piperidinyl)-2(1H)-quinazolinone and 100 g of pyridine hydrochloride was heated to 160° C. with stirring for 3 hours. After cooling, the product was dissolved in 500 mL of water, the solution obtained was carefully treated with excess solid sodium hydrogen carbonate, whereupon a highly viscous oil was precipitated. This oil was taken up in 150 mL of methanol, the methanolic solution formed was clarified over activated charcoal, then freed from solvent in vacuo once more. The residue was stirred with 50 mL of acetonitrile and then brought to the boil. It was left to cool and the precipitate formed was suction filtered and dried in vacuo at ambient temperature. Yield: 10.8 g (63% of theoretical). R$_f$=0.32 (MP F). IR (KBr): 1649 (C=O) cm$^{-1}$; MS: M$^+$=337.

EXAMPLE A11

3,4-dihydro-7-methoxy-3-(1-phenylmethyl-4-piperidinyl)-2(1H)-quinazolinone

A mixture of 2.5 g (7.682 mmol) of 2-amino-4-methoxy-N-(1-phenylmethyl-4-piperidinyl)-benzylamine, 1.62 g (10 mmol) of N,N'-carbonyldiimidazole, and 25 mL of dimethylformamide was heated to 90° C. with stirring for 2.5 hours. After cooling, the mixture was stirred into 100 mL of ice water, the suspension formed was overlaid with 10 mL of tert-butylmethylether, the precipitate formed was suction filtered, washed with water, and then with tert-butylmethylether. After drying in vacuo, 1.9 g (70% of theoretical) of colorless crystals were obtained. IR (KBr): 1664 (C=O) cm$^{-1}$; MS: M$^+$=351.

EXAMPLE A12

2-amino-4-methoxy-N-(1-phenylmethyl-4-piperidinyl)benzylamine

A solution of 3.2 g (9.003 mmol) of 4-methoxy-2-nitro-N-(1-phenylmethyl-4-piperidinyl)-benzylamine in 30 mL methanol was hydrogenated in the presence of 1 g of 10% rhodium charcoal for 5 hours at ambient temperature. The catalyst was filtered off and the filtrate was evaporated down in vacuo. 2.5 g (85% of theoretical) of a colorless, highly viscous oil was obtained, which was further processed without purification. R$_f$=0.34 (MP F). IR (KBr): no C=O; MS: M$^+$=325.

EXAMPLE A12

4-methoxy-2-nitro-N-(1-phenylmethyl-4-piperidinyl) benzylamine

A mixture of 3.0 g (16.561 mmol) of 4-methoxy-2-nitrobenzaldehyde, 3.2 g (16.817 mmol) of 1-phenylmethyl-4-piperidinamine and 30 mL of methanol was stirred for 2 hours at ambient temperature. Then 681 mg (18.0 mmol) of sodium borohydride was added and stirring was continued for one hour at ambient temperature. The mixture was stirred into 500 mL of ice water and carefully acidified with 10% hydrochloric acid. The solution obtained was washed twice with 50 mL of tert-butylmethylether, then made alkaline with 20% sodium hydroxide solution and extracted exhaustively with tert-butylmethylether. The final extracts obtained were combined, washed twice with 20 mL of water, dried over magnesium sulfate and evaporated down in vacuo. The colorless oil remaining was used in the next step without any further purification. Yield: 3.2 g (54% of theoretical). IR (KBr): no C=O; MS: M$^+$=355.

B. Preparation of the Final Compounds

EXAMPLE 1 cis-3-{1-[2-(4-chlorobenzoyl)cyclopropanecarbonyl]-4-piperidinyl}-3,4-dihydro-2(1H)-quinazolinone (Item No. 1)

A mixture of 1.0 g (4.452 mmol) of trans-2-(4-chlorobenzoyl)cyclopropanecarboxylic acid, 0.97 g (4.194 mmol) of 3,4-dihydro-3-(4-piperidinyl)-2(1H)-quinazolinone, 1.4 g (4.36 mmol) of TBTU, 0.455 mg (4.5 mmol) of triethylamine, and 20 mL of dimethylformamide was stirred for 5 hours at ambient temperature. The reaction mixture was freed from solvent in vacuo, diluted with 300 mL of water, and made slightly acidic with citric acid. The precipitate formed was suction filtered and carefully washed with water, then with 5 mL of tetrahydrofuran, and finally dried in a circulating air drier at a temperature of 60° C. 1.3 g (71% of theoretical) of a colorless crystalline product was obtained: m.p. 272° C.-273° C.; R$_f$0.24 (MP A); IR (KBr): 1674.1 cm$^{-1}$ (C=O); MS: M$^+$=437/439 (Cl).

The following were prepared analogously:

| Item No. | N | B | C | Remarks | % yield | El | R$_f$ | MS | IR [cm$^{-1}$] | m.p. [° C.] |
|---|---|---|---|---|---|---|---|---|---|---|
| 2 | N2 | B1 | C2 | THF as LM; DIEA as base | 49 | A | 0.63 | M$^+$ = 616/618/620 (Br$_2$); ESI: (M + H)$^+$ = 617/619/621 (Br$_2$) | 1684 (C=O) | colorless crystals |
| 3 | N2 | B1 | C2 | THF as LM; DIEA as base | 42 | A | 0.78 | M$^+$ = 574/576/578 (Br$_2$) | 1668 (C=O) | colorless crystals |
| 4 | N3 | B1 | C2 | DMF as LM; DIEA as base | 58 | D / A | 0.78 / 0.84 | M$^+$ = 652/654/656/658 (Br$_3$) | 1670 (C=O) | |
| 5 | N4 | B1 | C2 | DMF as LM; DIEA as base | 57 | A | 0.66 | ESI: (M + H)$^+$ = 587/589/591 (Br$_2$); (M + Na)$^+$ = 609/611/613 (Br$_2$) | 1684 (C=O) | |

-continued

| Item No. | N | B | C | Remarks | % yield | El | $R_f$ | MS | IR [cm$^{-1}$] | m.p. [° C.] |
|---|---|---|---|---|---|---|---|---|---|---|
| 6 | N5 | B1 | C2 | DMF as LM; DIEA as base | 26 | D A | 0.4 0.73 | M$^+$ = 654/656/658 (Br$_2$) | 3465, 3383 (NH, NH$_2$); 1685 (C=O); 1205, 1165, 1124 (CF$_3$) | |
| 7 | N6 | B1 | C2 | DMF as LM; DIEA as base | 31 | D A | 0.4 0.61 | M$^+$ = 602/604/606 (Br$_2$) | 1676 (C=O) | colorless crystals |
| 8 | N7 | B1 | C2 | DMF as LM; DIEA as base | 13 | D A | 0.7 0.73 | M$^+$ = 590/592/594 (Br$_2$) | 3379 (OH, NH); 1709, 1653 (C=O) | |
| 9 | N8 | B1 | C2 | DMF as LM; DIEA as base | 62 | D A | 0.5 0.74 | M$^+$ = 676/678/680 (Br$_2$) | 3460, 3332 (NH, NH$_2$); 1666 (C=O) | |
| 10 | N9 | B1 | C2 | THF as LM; DIEA as base | 52 | D A | 0.6 0.75 | M$^+$ = 654/656/658/660 (Br$_2$Cl$_2$) | 3462, 3383 (NH, NH$_2$); 1685 (C=O) | |
| 11 | N10 | B1 | C2 | THF as LM; DIEA as base | 65 | A | 0.36 | M$^+$ = 575/577/579 (Br$_2$) | 3444 (NH, NH$_2$); 1676 (C=O) | |
| 12 | N11 | B1 | C2 | DMF as LM; DIEA as base | 68 | D A | 0.75 0.69 | ESI: (M + H)$^+$ = 617/619/621 (Br$_2$); (M + Na)$^+$ = 639/641/643 (Br$_2$); (M + K)$^+$ = 655/657/659 (Br$_2$) | 1682 (C=O) | |
| 13 | N12 | B1 | C2 | DMF as LM; DIEA as base | 76 | D A | 0.7 0.75 | M$^+$ = 620/622/624 (Br$_2$, Cl) | 1684 (C=O) | |
| 14 | N13 | B1 | C2 | DMF as LM; DIEA as base | 63 | D A | 0.65 0.73 | M$^+$ = 631/633/635 (Br$_2$) | 3458, 3379 (NH, NH$_2$); 1684 (C=O) | |
| 15 | N14 | B1 | C2 | THF/DMF 1/1 v/v as LM; NEt$_3$ as base | 62 | G A | 0.39 0.52 | M$^+$ = 575/577/579 (Br$_2$) | 1668 (C=O) | colorless crystals |
| 16 | N15 | B1 | C2 | DMF as LM; DIEA as base | 24 | C | 0.20 | M$^+$ = 661/663/665 (Br$_2$) | 1666 (C=O) | 235 (AcOEt) |
| 17 | N16 | B1 | C2 | THF/DMF 1/1 v/v as LM; NEt$_3$ as base | 11 | C | 0.23 | M$^+$ = 672/674/676 (Br$_2$) | 1666 (C=O) | |
| 18 | N17 | B1 | C2 | DMF as LM; DIEA as base | 11 | A | 0.71 | M$^+$ = 654/656/658 (Br$_2$) | 3460, 3383 (NH, NH$_2$); 1687 (C=O) | 248 (AcOEt) |
| 19 | N18 | B1 | C2 | THF/DMF 10/1 v/v as LM; NEt$_3$ as base | 21 | C | 0.11 | M$^+$ = 675/677/679 (Br$_2$) | 1665 (C=O) | |
| 20 | N1 | B1 | C3 | THF as LM; DIEA as base | 48 | A | 0.58 | | 1657 (C=O) | colorless crystals |
| 21 | N4 | B1 | C3 | THF as LM; DIEA as base | 78 | | | M$^+$ = 587/589/591 (Br$_2$) | 1676 (C=O) | colorless crystals |
| 22 | N19 | B1 | C2 | THF/DMF 10/1 v/v as LM; NEt$_3$ as base | 50 | A | 0.69 | M$^+$ = 662/664/666 (Br$_2$) | 1739, 1666 (C=O) | colorless crystals |
| 24 | N21 | B1 | C2 | THF as LM; NEt$_3$ as base | 50 | A C | 0.15 0.85 | M$^+$ = 703/705/707 (Br$_2$) | 1664 (C=O) | |
| 25 | N22 | B1 | C2 | DMF as LM; NEt$_3$ as base | 76 | A | 0.74 | M$^+$ = 604/606/608 (Br$_2$) | 1666 (C=O) | colorless crystals |
| 26 | N23 | B1 | C2 | THF as LM; NEt$_3$ as base | 24 | A | 0.73 | M$^+$ = 662/664/666 (Br$_2$) | 3379 (NH, NH$_2$); 1755, 1668 (C=O) | colorless crystals |
| 28 | N25 | B1 | C2 | THF/DMF 10/1 v/v as LM; NEt$_3$ as base | 91 | A D | 0.78 0.75 | M$^+$ = 632/634/636 (Br$_2$) | 3454, 3379 (NH, NH$_2$); 1720, 1670 (C=O) | colorless crystals |
| 29 | N26 | B1 | C2 | DMF as LM; NEt$_3$ as base | 20 | A D | 0.60 0.75 | M$^+$ = 611/613/615 (Br$_2$) | 1730 (C=O) | colorless crystals |
| 30 | N27 | B1 | C2 | THF as LM; DIEA as base; from MeO$_2$CCH$_2$NH$_2$ HCl and N24-B1-C2 | 64 | A | 0.53 | M$^+$ = 689/691/693 (Br$_2$) | 1751, 1666 (C=O) | |
| 31 | N28 | B1 | C2 | THF as LM; DIEA as base; from Me$_2$NCH2CH$_2$NHCH$_3$ and N24-B1-C2 | 49 | C | 0.08 | M$^+$ = 702/704/706 (Br$_2$) | 1666 (C=O) | |

-continued

| Item No. | N | B | C | Remarks | % yield | El | $R_f$ | MS | IR [cm$^{-1}$] | m.p. [° C.] |
|---|---|---|---|---|---|---|---|---|---|---|
| 32 | N29 | B1 | C2 | THF as LM; DIEA as base; from Et$_2$NH and N24-B1-C2 | 20 | A D | 0.49 0.55 | M$^+$ = 673/675/677 (Br$_2$) | 1664 (C=O) | |
| 33 | N30 | B1 | C2 | THF as LM; DIEA as base; from (NH$_4$)$_2$CO$_3$ and N24-B1-C2 | 40 | A D | 0.31 0.48 | M$^+$ = 617/619/621 (Br$_2$) | 3363 (NH, NH$_2$); 1666 (C=O) | colorless crystals |
| 35 | N32 | B1 | C2 | THF as LM; DIEA as base | 57 | A | 0.70 | M$^+$ = 587/589/591 (Br$_2$); (M − H)$^-$ = 586/588/590 (Br$_2$); (M + Na)$^+$ = 610/612/614 (Br$_2$) | 3437, 3321 (NH$_2$, NH); 1684 (C=O) | |

EXAMPLE 2 trans-3-{1-[2-(4-amino-3,5-dibromobenzoyl)cyclopropanecarbonyl]-4-piperidinyl}-3,4-dihydro-6-(hydroxycarbonylmethoxy)-2(1H)-quinazolinone (Item No. 23)

A solution of 0.15 g (3.57 mmol) of lithium hydroxide hydrate in 10 mL of water was added to a solution of 0.6 g (0.903 mmol) of trans-3-{1-[2-(4-amino-3,5-dibromobenzoyl)cyclopropanecarbonyl]-4-piperidinyl}-3,4-dihydro-6-(methoxycarbonylmethoxy)-2(1H)-quinazolinone (Item No. 22) in a mixture of 10 mL of THF and 10 mL of methanol. After stirring for 14 hours at ambient temperature, the organic solvents were distilled off in vacuo and the residue remaining was combined with 3.6 mL of 1N hydrochloric acid. The precipitate formed was suction filtered and dried in vacuo at 30° C. The residue was taken up in tetrahydrofuran, the solution formed was filtered while hot and, after cooling, combined with diisopropyl ether until the precipitation reaction had ended. The precipitate was suction filtered. After drying in a circulating air drier 0.25 g (43% of theoretical) of colorless crystals were obtained. $R_f$ 0.63 (MP C); IR (KBr): 1730 cm$^{-1}$ (C=O); MS: ESI: (M−H+2Na)$^+$=693/695/697 (Br$_2$); (M−H)$^-$: 647/649/651 (Br$_2$); (M+Na)$^+$: 671/673/675 (Br$_2$).

The following were prepared analogously:

The Examples which follow illustrate the preparation of some pharmaceutical formulations which contain any desired compound of general formula (I) as active ingredient:

EXAMPLE I

Capsules for Powder Inhalation Containing 1 mg of Active Ingredient

Composition:

| 1 capsule for powder inhalation contains: | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with lactose. The mixture is transferred into hard gelatine capsules.

| Item No. | N | B | C | Remarks | % yield | El | $R_f$ | MS | IR [cm$^-$] | m.p. [° C.] |
|---|---|---|---|---|---|---|---|---|---|---|
| 27 | N24 | B1 | C2 | saponification of methyl ester Item No. 28 with NaOH in water/MeOH 1/1 (v/v) | 48 | C F | 0.51 0.5 | M$^+$ = 618/620/622 (Br$_2$); ESI: (M − H)$^-$ = 617/619/621 (Br$_2$) | 3379 (NH, NH$_2$); 1666 (C=O) | colorless crystals |
| 34 | N31 | B1 | C2 | saponification of methyl ester Item No. 30 with LiOH in water/THF 1/1 (v/v) | 73 | C F | 0.37 0.27 | ESI: (M − H + 2Na)$^+$ = 720/722/724 (Br$_2$); (M + Na)$^+$ = 698/700/702 (Br$_2$) | 1738, 1660 (C=O) | colorless crystals |

EXAMPLE II

Inhalable Solution for RESPIMAT® Containing 1 mg of Active Ingredient

Composition:

| 1 puff contains: | |
|---|---|
| active ingredient | 1.0 mg |
| benzalkonium chloride | 0.002 mg |
| disodium edetate | 0.0075 mg |
| purified water ad | 15.0 μL |

Method of Preparation:

The active ingredient and benzalkonium chloride are dissolved in water and transferred into RESPIMAT® cartridges.

EXAMPLE III

Inhalable Solution for Nebulizers Containing 1 mg of Active Ingredient

Composition:

| 1 vial contains: | |
|---|---|
| active ingredient | 0.1 g |
| sodium chloride | 0.18 g |
| benzalkonium chloride | 0.002 g |
| purified water ad | 20.0 mL |

Method of Preparation:

The active ingredient, sodium chloride and benzalkonium chloride are dissolved in water.

EXAMPLE IV

Propellant Gas-Operated Metering Aerosol Containing 1 mg of Active Ingredient

Composition:

| 1 puff contains: | |
|---|---|
| active ingredient | 1.0 mg |
| lecithin | 0.1% |
| propellant gas ad | 50.0 μL |

Method of Preparation:

The micronised active ingredient is homogeneously suspended in the mixture of lecithin and propellant gas. The suspension is transferred into a pressurised container with a metering valve.

EXAMPLE V

Nasal Spray Containing 1 mg of Active Ingredient

Composition:

| active ingredient | 1.0 mg |
|---|---|
| sodium chloride | 0.9 mg |
| benzalkonium chloride | 0.025 mg |
| disodium edetate | 0.05 mg |
| purified water ad | 0.1 mL |

Method of Preparation:

The active ingredient and the excipients are dissolved in water and transferred into a suitable container.

EXAMPLE VI

Injectable Solution Containing 5 mg of Active Substance per 5 mL

Composition:

| active substance | 5 mg |
|---|---|
| glucose | 250 mg |
| human serum albumin | 10 mg |
| glycofurol | 250 mg |
| water for injections ad | 5 mL |

Method of Preparation:

Glycofurol and glucose are dissolved in water for injections (WfI); human serum albumin is added; active ingredient is dissolved with heating; made up to specified volume with WfI; transferred into ampoules under nitrogen gas.

EXAMPLE VII

Injectable Solution Containing 100 mg of Active Substance per 20 mL

Composition:

| active substance | 100 mg |
|---|---|
| monopotassium dihydrogen phosphate ($KH_2PO_4$) | 12 mg |
| disodium hydrogen phosphate ($Na_2HPO_4 \cdot 2H_2O$) | 2 mg |
| sodium chloride | 180 mg |
| human serum albumin | 50 mg |
| Polysorbate 80 | 20 mg |
| water for injections ad | 20 mL |

Method of Preparation:

Polysorbate 80, sodium chloride, monopotassium dihydrogen phosphate, and disodium hydrogen phosphate are dissolved in water for injections (WfI); human serum albumin is added; active ingredient is dissolved with heating; made up to specified volume with WfI; transferred into ampoules.

EXAMPLE VIII

Lyophilisate Containing 10 mg of Active Substance

Composition:

| active substance | 10 mg |
| --- | --- |
| mannitol | 300 mg |
| human serum albumin | 20 mg |

Method of Preparation:

Mannitol is dissolved in water for injections (WfI); human serum albumin is added; active ingredient is dissolved with heating; made up to specified volume with WfI; transferred into vials; freeze-dried.

Solvent for Lyophilisate:

| Polysorbate 80 (Tween 80) | 20 mg |
| --- | --- |
| mannitol | 200 mg |
| water for injections ad | 10 mL |

Method of Preparation:

Polysorbate 80 and mannitol are dissolved in water for injections (WfI); transferred into ampoules.

EXAMPLE IX

Tablets Containing 20 mg of Active Substance

Composition:

| active substance | 20 mg |
| --- | --- |
| lactose | 120 mg |
| maize starch | 40 mg |
| magnesium stearate | 2 mg |
| Povidon K 25 | 18 mg |

Method of Preparation:

Active substance, lactose, and maize starch are homogeneously mixed; granulated with an aqueous solution of Povidone; mixed with magnesium stearate; compressed in a tablet press; weight of tablet 200 mg.

EXAMPLE X

Capsules Containing 20 mg Active Substance

Composition:

| active substance | 20 mg |
| --- | --- |
| maize starch | 80 mg |
| highly dispersed silica | 5 mg |
| magnesium stearate | 2.5 mg |

Method of Preparation:

Active substance, maize starch, and silica are homogeneously mixed; mixed with magnesium stearate; the mixture is packed into size 3 hard gelatine capsules in a capsule filling machine.

EXAMPLE XI

Suppositories Containing 50 mg of Active Substance

Composition:

| active substance | 50 mg |
| --- | --- |
| hard fat (Adeps solidus) q.s. ad | 1700 mg |

Method of Preparation:

Hard fat is melted at about 38° C.; ground active substance is homogeneously dispersed in the molten hard fat; after cooling to about 35° C. it is poured into chilled molds.

EXAMPLE XII

Injectable Solution Containing 10 mg of Active Substance per 1 mL

Composition:

| active substance | 10 mg |
| --- | --- |
| mannitol | 50 mg |
| human serum albumin | 10 mg |
| water for injections ad | 1 mL |

Method of Preparation:

Mannitol is dissolved in water for injections (WfI); human serum albumin is added; active ingredient is dissolved with heating; made up to specified volume with WfI; transferred into ampoules under nitrogen gas.

We claim:

1. A compound of general formula (I)

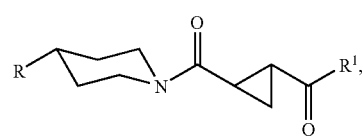

wherein:
R is a saturated or mono- or diunsaturated 5- to 7-membered aza, diaza, triaza, oxaza, thiaza, thiadiaza, or S,S-dioxido-thiadiaza heterocyclic group linked via a carbon or nitrogen atom, and
wherein the heterocyclic group of R:
(i) optionally contains one or two carbonyl groups adjacent to a nitrogen atom thereof,
(ii) is optionally substituted by an alkyl group at one of the nitrogen atoms, and
(iii) is optionally substituted at one or two carbon atoms thereof by identical or different substituent groups selected from:
(a) a straight-chain or branched alkyl group, or a phenyl, phenylmethyl, naphthyl, biphenylyl group, or
(b) a pyridinyl, diazinyl, furyl, thienyl, pyrrolyl, 1,3-oxazolyl, 1,3-thiazolyl, isoxazolyl, pyrazolyl, 1-methylpyrazolyl, imidazolyl, or 1-methylimidazolyl group,
wherein an olefinic double bond thereof is optionally fused with a benzene, pyridine, diazine, 1,3-oxazole, thiophene, furan, thiazole, pyrrole, N-methylpyrrole, quinoline, imidazole, or N-methylimidazole ring, and wherein the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl, or 1-methylimidazolyl groups contained in R and the benzo, thieno, pyrido- and diazino-fused heterocyclic groups in R are optionally independently additionally mono-, di-, or trisubstituted by:

(a) a fluorine, chlorine, or bromine atom, (b) an alkyl, dialkylaminoalkoxy, nitro, alkylthio, alkylsulfinyl, alkylsulfonyl, alkylsulfonylamino, phenyl, trifluoromethyl, alkoxycarbonyl, alkoxycarbonylalkyl, alkoxycarbonylalkoxy, hydroxycarbonylalkoxy, carboxy, carboxyalkyl, dialkyl-aminoalkyl, hydroxy, amino, acetylamino, propionylamino, aminocarbonyl, alkylaminocarbonyl, dialkylaminocarbonyl, [N-alkyl-N-(dialkylaminoalkyl)amino]carbonyl, [(hydroxycarbonylalkyl)amino]carbonyl, [(alkoxycarbonylalkyl)amino]carbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, aminocarbonylaminoalkyl, alkylaminocarbonylamino, alkanoyl, cyano, trifluoromethoxy, trifluoromethylthio, trifluoromethylsulfinyl, trifluoromethylsulfonyl, or $C_3$-$C_8$ cycloalkyl group, (c) a 4- to 8-membered alkyleneimino group wherein a methylene group in the 3-, 4-, or 5-position is optionally replaced by an oxygen atom or a methylimino group, or (d) an alkoxy group optionally substituted in the ω-position by a 5- to 7-membered heteroalicyclic group that is linked via a carbon or nitrogen atom and contains one or two heteroatoms not directly connected to each other selected from oxygen and nitrogen, wherein multiple substitution of the aforementioned phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl, or 1-methylimidazolyl groups contained in R and the benzo, thieno, pyrido- and diazino-fused heterocyclic groups in R by phenyl, $C_3$-$C_8$ cycloalkyl or 4- to 8-membered alkyleneimino groups is excluded; and $R^1$ is a phenyl, 1-naphthyl, 2-naphthyl, 1,2,3,4-tetrahydro-1-naphthyl, 1H-indol-3-yl, 1-methyl-1H-indol-3-yl, 1-formyl-1H-indol-3-yl, 4-imidazolyl, 1-methyl-4-imidazolyl, 2-thienyl, 3-thienyl, thiazolyl, 1H-indazol-3-yl, 1-methyl-1H-indazol-3-yl, benzo[b]fur-3-yl, benzo[b]thien-3-yl, pyridinyl, quinolinyl, or isoquinolinyl group, wherein each group of $R^1$ is optionally independently mono-, di-, or trisubstituted by a substituent group selected from:

(a) a fluorine, chlorine, or bromine atom, (b) a branched or unbranched alkyl, $C_3$-$C_8$ cycloalkyl, phenylalkyl, alkenyl, alkoxy, phenyl, phenylalkoxy, trifluoromethyl, alkoxycarbonylalkyl, carboxyalkyl, alkoxycarbonyl, carboxy, dialkylaminoalkyl, dialkylaminoalkoxy, nitro, hydroxy, amino, acetylamino, propionylamino, methylsulfonyloxy, aminocarbonyl, alkylaminocarbonyl, dialkylaminocarbonyl, alkanoyl, cyano, tetrazolyl, phenyl, pyridinyl, thiazolyl, furyl, trifluoromethoxy, trifluoromethylthio, trifluoromethylsulfinyl, or trifluoromethylsulfonyl group, wherein the hydroxy, amino, indolyl and imidazolyl groups contained in the abovementioned groups are each optionally independently substituted by a protecting group selected from:

(a) a phenylalkoxycarbonyl group with 1 to 3 carbon atoms in the alkoxy moiety optionally substituted in the phenyl nucleus by a halogen atom, a nitro or phenyl group, or one or two methoxy groups, (b) an alkoxycarbonyl group having a total of 1 to 5 carbon atoms in the alkyl moiety, or (c) a formyl, acetyl, trifluoroacetyl, allyloxycarbonyl, 2,2, 2-trichloro-(1,1-dimethylethoxy)carbonyl, or 9-fluorenylmethoxycarbonyl group, wherein all the abovementioned alkyl and alkoxy groups and the alkyl or alkylene moieties present within the other groups specified contain 1 to 5 carbon atoms, unless otherwise stated, or a diastereomer, enantiomer, or salt thereof.

2. The compound of general formula (I) according to claim 1, wherein the protecting group is selected from: a formyl, acetyl, trifluoroacetyl, methoxycarbonyl, ethoxycarbonyl, n-propoxycarbonyl, isopropoxycarbonyl, n-butoxycarbonyl, 1-methylpropoxycarbonyl, 2-methylpropoxycarbonyl, tert-butyloxycarbonyl, benzyloxycarbonyl, 2-nitrobenzyloxycarbonyl, 4-nitrobenzyloxycarbonyl, 4-methoxybenzyloxy-carbonyl, 2-chlorobenzyloxycarbonyl, 3-chlorobenzyloxycarbonyl, 4-chlorobenzyloxycarbonyl, 4-biphenylyl-α,α-dimethylbenzyloxycarbonyl, allyloxycarbonyl, 3,5-dimethoxy -α,α-dimethylbenzyloxycarbonyl, 2,2, 2-trichloro-(1,1-dimethylethoxy)carbonyl, or 9-fluorenylmethoxycarbonyl group.

3. The compound of general formula (I) according to claim 1, wherein:

R is a mono- or diunsaturated 5- to 7-membered aza, diaza, triaza, or thiaza heterocyclic group linked via a carbon or nitrogen atom, and wherein the heterocyclic group of R:

(i) optionally contains one or two carbonyl groups adjacent to a nitrogen atom thereof, and (ii) is optionally substituted at one or two carbon atoms thereof by identical or different substituent groups selected from:

(a) a phenyl group, or (b) a pyridinyl, diazinyl, thienyl, pyrrolyl, 1,3-thiazolyl, isoxazolyl, pyrazolyl, or 1-methylpyrazolyl group, wherein an olefinic double bond thereof is optionally fused with a benzene, pyridine, diazine, or quinoline ring, and wherein the phenyl, pyridinyl, diazinyl, thienyl, pyrrolyl, 1,3-thiazolyl, isoxazolyl, pyrazolyl, or 1-methylpyrazolyl, groups contained in R and the benzo, thieno, pyrido- and diazino-fused heterocyclic groups in R are optionally independently additionally mono-, di-, or trisubstituted by:

(a) a fluorine, chlorine, or bromine atom, (b) an alkyl, dialkylaminoalkoxy, nitro, trifluoromethyl, alkoxycarbonyl, alkoxycarbonylalkyl, alkoxycarbonylalkoxy, hydroxycarbonylalkoxy, carboxy, carboxyalkyl, dialkylaminoalkyl, hydroxy, amino, acetylamino, propionylamino, aminocarbonyl, alkylaminocarbonyl, dialkylaminocarbonyl, [N-alkyl-N-(dialkylaminoalkyl)amino]carbonyl, [(hydroxycarbonylalkyl)amino]carbonyl, [(alkoxy-carbonylalkyl)amino]carbonyl, aminocarbonylamino, aminocarbonylaminoalkyl, alkylaminocarbonylamino, alkanoyl, or trifluoromethoxy group, (c) a 4- to 7-membered alkyleneimino group wherein a methylene group in the 3-, 4-, or 5-position is optionally replaced by an oxygen atom or a methylimino group, or (d) an alkoxy group optionally substituted in the ω-position by a 5- to 7-membered heteroalicyclic group that is linked via a carbon or nitrogen atom and contains one or two heteroatoms not directly connected to each other selected from oxygen and nitrogen, wherein multiple substitution of the aforementioned phenyl, pyridinyl, diazinyl, thienyl, pyrrolyl, 1,3-thiazolyl, isoxazolyl, pyrazolyl or 1-methylpyrazolyl groups contained in R and the benzo, thieno, pyrido- and diazino-fused heterocyclic groups in R by 4- to 7-membered alkyleneimino groups is excluded; and $R^1$ is a phenyl, 1-naphthyl, or 2-naphthyl group, wherein each group of $R^1$ is optionally independently mono-, di-, or trisubstituted by a substituent group selected from:
(a) a fluorine, chlorine, or bromine atom, or
(b) a branched or unbranched alkyl, alkoxy, trifluoromethyl, nitro, hydroxy, amino, or acetylamino group, wherein all the abovementioned alkyl and alkoxy groups and the alkyl or alkylene moieties present within the other groups specified contain 1 to 4 carbon atoms, unless otherwise stated, or a diastereomer, enantiomer, or salt thereof.

4. The compound of general formula (I) according to claim 1, wherein:

R is a mono- unsaturated 5- to 7-membered diaza or triaza heterocyclic group linked via a carbon or nitrogen atom, and wherein the heterocyclic group of R:
(i) optionally contains one carbonyl group adjacent to a nitrogen atom thereof, and
(ii) is optionally substituted at one carbon atom thereof by a phenyl group, or an olefinic double bond of one of the above-mentioned unsaturated heterocyclic groups in R are optionally fused with a benzene, pyridine or quinoline ring, and wherein the phenyl groups contained in R and the benzo- and pyrido-fused heterocyclic groups in R are optionally independently additionally mono-, di-, or trisubstituted by:
(a) a fluorine, chlorine, or bromine atom,
(b) an alkyl, dialkylaminoalkoxy, nitro, trifluoromethyl, alkoxycarbonyl, alkoxycarbonylalkoxy, hydroxycarbonylalkoxy, carboxy, hydroxy, aminocarbonyl, alkylaminocarbonyl, dialkylaminocarbonyl, [N-alkyl-N-(dialkylaminoalkyl)amino]carbonyl, [(hydroxycarbonylalkyl)amino]carbonyl, [(alkoxycarbonylalkyl)amino]carbonyl, alkanoyl, or trifluoromethoxy group,
(c) a 5- to 7-membered alkyleneimino group wherein a methylene group in the 3- or 4-position is optionally replaced by an oxygen atom or a methylimino group, or
(d) an alkoxy group optionally substituted in the o-position by a 5- or 6-membered heteroalicyclic group, wherein the heteroalicyclic group is linked via a carbon atom and contains an oxygen atom in each of the 2- and 2'-positions or is linked via a carbon or nitrogen atom and contains one or two nitrogen atoms not directly linked to one another or an oxygen and a nitrogen atom which are separated from each other by at least one methylene group, wherein multiple substitution of phenyl groups contained in R and the benzo- and pyrido-fused heterocyclic groups in R by 5- to 7-membered alkyleneimino groups is excluded; and $R^1$ is a phenyl group optionally independently mono-, di-, or trisubstituted by a substituent group selected from:
(a) a fluorine, chlorine, or bromine atom, or
(b) an alkoxy, trifluoromethyl, nitro, hydroxy, or amino group, wherein all the abovementioned alkyl and alkoxy groups and the alkyl or alkylene moieties present within the other groups specified contain 1 to 3 carbon atoms, unless otherwise stated, or a diastereomer, enantiomer, or salt thereof.

5. A compound of general formula (I)

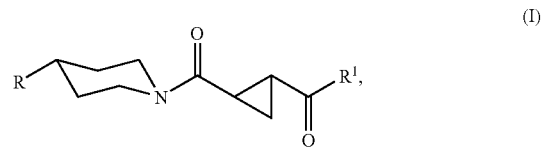

(I)

wherein:

R is a 3,4-dihydro-2(1H)-oxoquinazolin-3-yl, 1,3-dihydro-4-phenyl-2H-2-oxoimidazol-1-yl, 2,4-dihydro-5-phenyl-3(3H)-oxo-1,2,4-triazol-2-yl, 3,4-dihydro-2(1H)-oxopyrido[4,3-d]pyrimidin-3-yl, 3,4-dihydro-2(1H)-oxopyrido[3,4-d]pyrimidin-3-yl, or 1,3-dihydro-2(2H)-oxoimidazo[4,5-c]quinolin-3-yl group, and wherein the mono- and bicyclic heterocyclic groups in R are optionally independently additionally:
(a) mono-, or di-substituted by a fluorine, chlorine, or bromine atom, or
(b) monosubstituted by a 4-methyl-1-piperazinyl, 2,5-dioxacyclopentylmethoxy, nitro, hydroxy, methoxy, 2-(4-morpholinyl)ethoxy, 2-dimethylaminoethoxy, 3-dimethylaminopropoxy, methoxycarbonylmethoxy, hydroxycarbonylmethoxy, trifluoromethyl, methoxycarbonyl, carboxy, aminocarbonyl, diethylaminocarbonyl, [N-(2-dimethylaminoethyl)-N-methylamino]carbonyl, [(methoxycarbonylmethyl)amino]carbonyl, or [(hydroxycarbonylmethyl)amino]carbonyl group; and $R^1$ is a phenyl group optionally independently mono-, di-, or trisubstituted by a substituent group selected from:
(a) a fluorine, chlorine, or bromine atom, or
(b) a hydroxy or amino group, or a diastereomer, enantiomer, or salt thereof.

6. A compound selected from the group consisting of:
(a) cis-3-{1-[2-(4-chlorobenzoyl)cyclopropanecarbonyl]-4-piperidinyl}-3,4-dihydro-2(1H)-quinazolinone;
(b) trans-1-{1-[2-(4-amino-3,5-dibromobenzoyl)cyclopropanecarbonyl]-4-piperidinyl}-1,3-dihydro-4-(3-methoxyphenyl)-2(2H)-imidazolone;
(c) trans-3-{1-[2-(4-amino-3,5-dibromobenzoyl)cyclopropanecarbonyl]-4-piperidinyl}-3,4-dihydro-2(1H)-quinazolinone;
(d) trans-3-{1-[2-(4-amino-3,5-dibromobenzoyl)cyclopropanecarbonyl]-4-piperidinyl}-6-bromo-3,4-dihydro-2(1H)-quinazolinone;
(e) trans-1-{1-[2-(4-amino-3,5-dibromobenzoyl)cyclopropanecarbonyl]-4-piperidinyl}-1,3-dihydro-4-phenyl-2(2H)-imidazolone;

(f) trans-1-{1-[2-(4-amino-3,5-dibromobenzoyl)cyclopropanecarbonyl]-4-piperidinyl}-1,3-dihydro-4-[3-(trifluoromethyl)phenyl]-2(2H)-imidazolone;
(g) trans-1-{1-[2-(4-amino-3,5-dibromobenzoyl)cyclopropanecarbonyl]-4-piperidinyl}-1,3-dihydro-4-(3-hydroxyphenyl)-2(2H)-imidazolone;
(h) trans-3-{1-[2-(4-amino-3,5-dibromobenzoyl)cyclopropanecarbonyl]-4-piperidinyl}-3,4-dihydro-6-hydroxy-2(1H)-quinazolinone;
(i) trans-3-{1-[2-(4-amino-3,5-dibromobenzoyl)cyclopropanecarbonyl]-4-piperidinyl}-3,4-dihydro-6-[(1,3-dioxolan-2-yl)methoxy]-2(1H)-quinazolinone;
(j) trans-1-{1-[2-(4-amino-3,5-dibromobenzoyl)cyclopropanecarbonyl]-4-piperidinyl}-4-(3,4-dichlorophenyl)-1,3-dihydro-2(2H)-imidazolone;
(k) trans-3-{1-[2-(4-amino-3,5-dibromobenzoyl)cyclopropanecarbonyl]-4-piperidinyl}-3,4-dihydro-2(1H)-pyrido[4,3-d]pyrimidinone;
(l) trans-1-{1-[2-(4-amino-3,5-dibromobenzoyl)cyclopropanecarbonyl]-4-piperidinyl}-1,3-dihydro-4-(2-methoxyphenyl)-2(2H)-imidazolone;
(m) trans-1-{1-[2-(4-amino-3,5-dibromobenzoyl)cyclopropanecarbonyl]-4-piperidinyl}-4-(3-chlorophenyl)-1,3-dihydro-2(2H)-imidazolone;
(n) trans-1-{1-[2-(4-amino-3,5-dibromobenzoyl)cyclopropanecarbonyl]-4-piperidinyl}-1,3-dihydro-4-(3-nitrophenyl)-2(2H)-imidazolone;
(o) trans-3-{1-[2-(4-amino-3,5-dibromobenzoyl)cyclopropanecarbonyl]-4-piperidinyl}-3,4-dihydro-2(1H)-pyrido[3,4-d]pyrimidinone;
(p) trans-3-{1-[2-(4-amino-3,5-dibromobenzoyl)cyclopropanecarbonyl]-4-piperidinyl}-3,4-dihydro-6-[2-(dimethylamino)ethoxy]-2(1H)-quinazolinone;
(q) trans-3-{1-[2-(4-amino-3,5-dibromobenzoyl)cyclopropanecarbonyl]-4-piperidinyl}-3,4-dihydro-6-(4-methyl-1-piperazinyl)-2(1H)-quinazolinone;
(r) trans-1-{1-[2-(4-amino-3,5-dibromobenzoyl)cyclopropanecarbonyl]-4-piperidinyl}-1,3-dihydro-4-[2-(trifluoromethyl)phenyl]-2(2H)-imidazolone;
(s) trans-3-{1-[2-(4-amino-3,5-dibromobenzoyl)cyclopropanecarbonyl]-4-piperidinyl}-3,4-dihydro-6-[3-(dimethylamino)propoxy]-2(1H)-quinazolinone;
(t) trans-3-{1-[2-(3,5-dibromo-4-hydroxybenzoyl)cyclopropanecarbonyl]-4-piperidinyl}-3,4-dihydro-2(1H)-quinazolinone;
(u) trans-1-{1-[2-(3,5-dibromo-4-hydroxybenzoyl)cyclopropanecarbonyl]-4-piperidinyl}-1,3-dihydro-4-phenyl-2(2H)-imidazolone;
(v) trans-3-{1-[2-(4-amino-3,5-dibromobenzoyl)cyclopropanecarbonyl]-4-piperidinyl}-3,4-dihydro-6-(methoxycarbonylmethoxy)-2(1H)-quinazolinone;
(w) trans-3-{1-[2-(4-amino-3,5-dibromobenzoyl)cyclopropanecarbonyl]-4-piperidinyl}-3,4-dihydro-6-(hydroxycarbonylmethoxy)-2(1H)-quinazolinone;
(x) trans-3-{1-[2-(4-amino-3,5-dibromobenzoyl)cyclopropanecarbonyl]-4-piperidinyl}-3,4-dihydro-6-[2-(4-morpholinyl)ethoxy]-2(1H)-quinazolinone;
(y) trans-3-{1-[2-(4-amino-3,5-dibromobenzoyl)cyclopropanecarbonyl]-4-piperidinyl}-3,4-dihydro-7-methoxy-2(1H)-quinazolinone;
(z) trans-3-{1-[2-(4-amino-3,5-dibromobenzoyl)cyclopropanecarbonyl]-4-piperidinyl}-3,4-dihydro-7-(methoxycarbonylmethoxy)-2(1H)-quinazolinone;
(aa) trans-3-{1-[2-(4-amino-3,5-dibromobenzoyl)cyclopropanecarbonyl]-4-piperidinyl}-7-carboxy-3,4-dihydro-2(1H)-quinazolinone;
(ab) trans-3-{1-[2-(4-amino-3,5-dibromobenzoyl)cyclopropanecarbonyl]-4-piperidinyl}-7-methoxycarbonyl-3,4-dihydro-2(1H)-quinazolinone;
(ac) trans-3-{1-[2-(4-amino-3,5-dibromobenzoyl)cyclopropanecarbonyl]-4-piperidinyl}-1,3-dihydro-2(2H)-imidazo[4,5-c]quinolinone;
(ad) trans-3-{1-[2-(4-amino-3,5-dibromobenzoyl)cyclopropanecarbonyl]-4-piperidinyl}-3,4-dihydro-7-{[(methoxycarbonylmethyl)amino]carbonyl}-2(1H)-quinazolinone;
(ae) trans-3-{1-[2-(4-amino-3,5-dibromobenzoyl)cyclopropanecarbonyl]-4-piperidinyl}-3,4-dihydro-7-{[N-(2-dimethylaminoethyl)-N-methylamino]carbonyl}-2(1H)-quinazolinone;
(af) trans-3-{1-[2-(4-amino-3,5-dibromobenzoyl)cyclopropanecarbonyl]-4-piperidinyl}-7-diethylaminocarbonyl-3,4-dihydro-2(1H)-quinazolinone;
(ag) trans-7-aminocarbonyl-3-{1-[2-(4-amino-3,5-dibromobenzoyl)cyclopropanecarbonyl]-4-piperidinyl}-3,4-dihydro-2(1H)-quinazolinone;
(ah) trans-3-{1-[2-(4-amino-3,5-dibromobenzoyl)cyclopropanecarbonyl]-4-piperidinyl}-3,4-dihydro-7-{[(hydroxycarbonylmethyl)amino]carbonyl}-2(1H)-quinazolinone; and
(ai) trans-1-{1-[2-(4-amino-3,5-dibromobenzoyl)cyclopropanecarbonyl]-4-piperidinyl}-2,4-dihydro-5-phenyl-3(3H)1,2,4-triazolone,
or a salt thereof.

7. A compound selected from the group consisting of:
(a) trans-1-{1-[2-(4-amino-3,5-dibromobenzoyl)cyclopropanecarbonyl]-4-piperidinyl}-1,3-dihydro-4-(3-methoxyphenyl)-2(2H)-imidazolone;
(b) trans-3-{1-[2-(4-amino-3,5-dibromobenzoyl)cyclopropanecarbonyl]-4-piperidinyl}-3,4-dihydro-2(1H)-quinazolinone;
(c) trans-1-{1-[2-(4-amino-3,5-dibromobenzoyl)cyclopropanecarbonyl]-4-piperidinyl}-1,3-dihydro-4-phenyl-2(2H)-imidazolone;
(d) trans-1-{1-[2-(4-amino-3,5-dibromobenzoyl)cyclopropanecarbonyl]-4-piperidinyl}-1,3-dihydro-4-(3-hydroxyphenyl)-2(2H)-imidazolone;
(e) trans-3-{1-[2-(4-amino-3,5-dibromobenzoyl)cyclopropanecarbonyl]-4-piperidinyl}-3,4-dihydro-6-hydroxy-2(1H)-quinazolinone;
(f) trans-3-{1-[2-(4-amino-3,5-dibromobenzoyl)cyclopropanecarbonyl]-4-piperidinyl}-3,4-dihydro-6-[(1,3-dioxolan-2-yl)methoxy]-2(1H)-quinazolinone;
(g) trans-1-{1-[2-(4-amino-3,5-dibromobenzoyl)cyclopropanecarbonyl]-4-piperidinyl}-4-(3-chlorophenyl)-1,3-dihydro-2(2H)-imidazolone;
(h) trans-3-{1-[2-(4-amino-3,5-dibromobenzoyl)cyclopropanecarbonyl]-4-piperidinyl}-3,4-dihydro-6-[3-(dimethylamino)propoxy]-2(1H)-quinazolinone;
(i) trans-3-{1-[2-(4-amino-3,5-dibromobenzoyl)cyclopropanecarbonyl]-4-piperidinyl}-3,4-dihydro-6-(methoxycarbonylmethoxy)-2(1H)-quinazolinone;
(j) trans-3-{1-[2-(4-amino-3,5-dibromobenzoyl)cyclopropanecarbonyl]-4-piperidinyl}-3,4-dihydro-6-(hydroxycarbonylmethoxy)-2(1H)-quinazolinone; and
(k) trans-1-{1-[2-(4-amino-3,5-dibromobenzoyl)cyclopropanecarbonyl]-4-piperidinyl}-2,4-dihydro-5-phenyl-3(3H)-1,2,4-triazolone,
or a salt thereof.

8. The physiologically acceptable salt of the compound according to claim 1.

9. The physiologically acceptable salt of the compound according to claim 2.

10. The physiologically acceptable salt of the compound according to claim 3.

11. The physiologically acceptable salt of the compound according to claim 4.

12. The physiologically acceptable salt of the compound according to claim 5.

13. The physiologically acceptable salt of the compound according to claim 6.

14. The physiologically acceptable salt of the compound according to claim 7.

15. A pharmaceutical composition comprising a compound according to claim 1 or a physiologically acceptable salt thereof and one or more inert carriers and/or diluents.

16. A pharmaceutical composition comprising a compound according to claim 2 or a physiologically acceptable salt thereof and one or more inert carriers and/or diluents.

17. A pharmaceutical composition comprising a compound according to claim 3 or a physiologically acceptable salt thereof and one or more inert carriers and/or diluents.

18. A pharmaceutical composition comprising a compound according to claim 4 or a physiologically acceptable salt thereof and one or more inert carriers and/or diluents.

19. A pharmaceutical composition comprising a compound according to claim 5 or a physiologically acceptable salt thereof and one or more inert carriers and/or diluents.

20. A pharmaceutical composition comprising a compound according to claim 6 or a physiologically acceptable salt thereof and one or more inert carriers and/or diluents.

21. A pharmaceutical composition comprising a compound according to claim 7 or a physiologically acceptable salt thereof and one or more inert carriers and/or diluents.

22. A method of treating headache in a patient in need thereof, the method comprising administering to the patent a therapeutically effective amount the compound according to claim 1.

23. A method of treating headache in a patient in need thereof, the method comprising administering to the patent a therapeutically effective amount the compound according to claim 2.

24. A method of treating headache in a patient in need thereof, the method comprising administering to the patent a therapeutically effective amount the compound according to claim 3.

25. A method of treating headache in a patient in need thereof, the method comprising administering to the patent a therapeutically effective amount the compound according to claim 4.

26. A method of treating headache in a patient in need thereof, the method comprising administering to the patent a therapeutically effective amount the compound according to claim 5.

27. A method of treating headache in a patient in need thereof, the method comprising administering to the patent a therapeutically effective amount the compound according to claim 6.

28. A method of treating headache in a patient in need thereof, the method comprising administering to the patent a therapeutically effective amount the compound according to claim 7.

* * * * *